US008985113B2

(12) United States Patent
Aldana

(10) Patent No.: US 8,985,113 B2
(45) Date of Patent: Mar. 24, 2015

(54) HANDHELD THERAPEUTIC GAS DELIVERY

(71) Applicant: Mark W. Aldana, Lubbock, TX (US)

(72) Inventor: Mark W. Aldana, Lubbock, TX (US)

(*) Notice: Subject to any disclaimer, the term of this patent is extended or adjusted under 35 U.S.C. 154(b) by 8 days.

(21) Appl. No.: 14/095,301

(22) Filed: Dec. 3, 2013

(65) Prior Publication Data
US 2014/0090644 A1 Apr. 3, 2014

Related U.S. Application Data

(63) Continuation-in-part of application No. PCT/US2012/062193, filed on Oct. 26, 2012.

(60) Provisional application No. 61/552,253, filed on Oct. 27, 2001.

(51) Int. Cl.
A62B 9/02 (2006.01)
B65D 83/00 (2006.01)
B65D 83/14 (2006.01)
B65D 83/18 (2006.01)
A61M 16/12 (2006.01)
A61M 16/10 (2006.01)
A61M 16/20 (2006.01)
A61M 16/06 (2006.01)

(52) U.S. Cl.
CPC ............... *A61M 16/12* (2013.01); *A61M 16/10* (2013.01); *A61M 16/20* (2013.01); *A61M 16/06* (2013.01); *A61M 16/105* (2013.01); *A61M 2202/0208* (2013.01); *A61M 2202/0225* (2013.01); *A61M 2202/025* (2013.01); *A61M 2202/0283* (2013.01); *A61M 2202/0291* (2013.01); *A61M 2202/048* (2013.01); *A61M 2205/8225* (2013.01)
USPC ............. 128/205.24; 128/204.18; 222/402.13

(58) Field of Classification Search
CPC . A61M 16/00; A61M 16/06; A61M 16/0683; A61M 16/08; A61M 16/0816; A61M 16/0875; A61M 16/20; A61M 16/0605; A61M 5/00; A61M 5/0086; A61M 5/009; A61M 2210/0606; A61M 2210/0618; A62B 9/00; A62B 9/02; A62B 7/00; A62B 7/02; A62B 7/04
USPC ............. 128/200.24, 200.26, 202.27, 204.18, 128/205.25, 205.11, 205.12, 205.24, 128/205.27, 205.29, 206.12, 206.18, 128/206.21; 239/600; 222/3, 5, 402.13, 222/402.15, 505, 507, 517
See application file for complete search history.

(56) References Cited

U.S. PATENT DOCUMENTS 2,087,119 A * 7/1937 Rosenow et al. ........ 128/205.25
2,676,060 A 4/1954 Montenier
(Continued)

Primary Examiner — Justine Yu
Assistant Examiner — Michael Tsai
(74) Attorney, Agent, or Firm — CARR Law Firm PLLC

(57) ABSTRACT

A nozzle apparatus for dispensing an adjustable combination of gas, having a nozzle outlet adjustably combined with a delivery component. The nozzle outlet may have a groove for receiving a roll pin; and an inner lumen comprising a cylindrical shaft having a diameter between 5/1000ths and 20/1000ths of an inch. The delivery component configured to receive air from the nozzle outlet, may have a first circular ambient air hole having a diameter, and a second circular ambient air hole having the same diameter as the first ambient air hole, and a removable plugging device covering the second circular ambient air hole. The delivery component may be adjustable in orientation with respect to the nozzle outlet, and may be adjustable to vary a concentration of therapeutic gas delivered to a patient.

30 Claims, 16 Drawing Sheets

(56) References Cited

U.S. PATENT DOCUMENTS

| | | | | |
|---|---|---|---|---|
| 3,836,079 | A | 9/1974 | Huston | |
| 4,054,622 | A | 10/1977 | Lester | |
| 4,119,097 | A | 10/1978 | Spector | |
| 4,274,404 | A * | 6/1981 | Molzan et al. | 128/204.25 |
| 4,582,054 | A | 4/1986 | Ferrer | |
| 4,643,183 | A * | 2/1987 | Seilinger | 128/204.17 |
| 5,207,221 | A * | 5/1993 | Stulbach | 128/206.29 |
| 5,524,613 | A | 6/1996 | Haber et al. | |
| 5,553,758 | A * | 9/1996 | Melendy et al. | 222/533 |
| 5,846,556 | A | 12/1998 | Brooks | |
| 6,016,801 | A | 1/2000 | Philips | |
| 6,125,844 | A | 10/2000 | Samiotes | |
| 6,311,793 | B1 * | 11/2001 | Larsen et al. | 175/340 |
| 6,708,692 | B2 | 3/2004 | Lee et al. | |
| 6,712,070 | B2 | 3/2004 | Drachmann et al. | |
| 6,981,660 | B2 | 1/2006 | Piper | |
| 7,021,392 | B2 * | 4/2006 | Bentzien et al. | 169/37 |
| 7,051,731 | B1 | 5/2006 | Rogerson | |
| 7,163,130 | B2 | 1/2007 | Lafond | |
| 7,299,802 | B2 * | 11/2007 | Feldman | 128/204.18 |
| 7,461,649 | B2 | 12/2008 | Gamard et al. | |
| 7,681,572 | B2 | 3/2010 | Fishman | |
| 7,874,292 | B2 * | 1/2011 | Smith et al. | 128/206.27 |
| 2006/0196510 | A1 | 9/2006 | McDonald et al. | |
| 2007/0235029 | A1 | 10/2007 | Zhu et al. | |
| 2008/0078382 | A1 | 4/2008 | LeMahieu et al. | |
| 2008/0178875 | A1 * | 7/2008 | Henry | 128/201.22 |
| 2009/0071474 | A1 | 3/2009 | Fishman | |
| 2011/0046546 | A1 | 2/2011 | Rasor et al. | |

* cited by examiner

HANDHELD THERAPEUTIC GAS DELIVERY

CROSS-REFERENCE TO RELATED APPLICATIONS

This application is a continuation-in-part of, and claims the benefit of the filing date of, co-pending PCT patent application no. PCT/US2012/062193 entitled HANDHELD THERAPEUTIC GAS DELIVERY, filed Oct. 26, 2012, the entire contents of which are incorporated herein by reference for all purposes.

TECHNICAL FIELD

The disclosed concept relates generally to therapeutic gas delivery devices and methods and, more specifically, a handheld portable device to deliver an immediate mild therapeutic gas to a person or mammal in distress or experiencing undesirable symptoms.

BACKGROUND

The delivery of therapeutic gases to treat a medical condition or symptom is, in its broadest sense, generally known. The most common known application is the delivery of oxygen via nasal cannula to patients. Other commonly recognized therapeutic gases include oxygen, nitrous oxide, xenon, helium, carbon dioxide and various combinations of each, also usually delivered by nasal cannula. With the exception of oxygen, which is frequently prescribed for home use, most of these gases are only delivered in highly controlled medical settings using large volume gas cylinders.

There do not appear to be any products on the market for the self-administration of portable handheld therapeutic gases with the exception of devices that deliver quick "blasts" of oxygen, intended specifically for those performing sports activities in high elevation settings.

There are a handful of patents and published applications describing aspects of the administration of smaller doses of therapeutic gases, however they all differ greatly from the disclosed device and method.

U.S. Pat. No. 6,712,070 describes an inhalation device for a person suffering from asthma or bronchospasm where the outlet valve of the gas canister is adapted to be activated by the inhalation of the person independent of the activation of the gas canister. U.S. Pat. No. 7,461,649 describes a portable gas operating inhaler which incorporates a drug storage chamber such that the compressed gas fluidizes and aerosolizes the drug to produce a drug cloud. U.S. Pat. No. 5,846,556 describes an inhalant composition for reducing stress that incorporates nitrogen, oxygen, an inert gas, carbon dioxide, and an anesthetic agent present in a proportion insufficient to produce anesthesia. The described use is primarily for cigarette smoking cessation.

U.S. Pat. No. 6,125,844 describes a portable gas-assisted dispensing of medication not using a fluorocarbon propellant. U.S. Pub. No. 2011/0046546 describes a dispenser for carbon dioxide to deliver small volumes of the gases to patients in a manner where the gas infuses into a body region in order to bathe the mucous membranes. U.S. Pat. No. 6,016,801 describes a nitrous oxide delivery system wherein nitrous oxide flows when the user bites on a rear mouthpiece, the nitrous being used for a calming effect for going through cigarette cessation. U.S. Patent 2009/0071474 describes a complex apparatus for administering small volumes of medical gases, the apparatus having a housing, a cassette, gas cartridges and a patient supply interface. It further includes such elements as a gas sensor, a blender chamber, a first valve, a second valve, a mounting means and a radio chip, all designed for delivery of smaller doses of therapeutic gases but limited to healthcare inpatient or outpatient settings.

It is common for persons to take mild oral sedatives such as Valium prior to stressful encounters such as a surgical procedure. Oral sedatives have a variety of disadvantages in that they take several minutes to an hour to achieve their desired effect, their effect may last longer than the person needs and, because they are metabolized through the digestive system, liver and kidneys, the drugs may cause nausea, vomiting, or other undesirable symptoms. In settings where sedatives must be given to calm combative patients, oral medications cannot usually be given as they are too difficult, or take too long, to administer. In that environment, often intravenous, intramuscular, or subcutaneous injections of sedatives or other drugs are administered (such as Propofol or Zolam). There are disadvantages associated with injections or IVs. For one, a sharp needle is employed, which, during the resulting tussle with a combative person can strike unintended targets. The needle can cause unnecessary bleeding and/or pain to the recipient. This type of administration can take several minutes to achieve its effect. There is a need for a handheld method and device to administer an immediate, painless, therapeutic effect that is minimal in side effects and is short acting.

None of the described prior art solves the problem of how to deliver an immediate mild or moderate sedative or anesthesia, pain reliever, pain tolerance enhancer or other therapeutic agent to a voluntary or involuntary recipient in a variety of medical, ambulatory, or even non-medical settings. None of the described prior art describes a handheld portable delivery device for the immediate administration by a licensed professional or individual to self-administer a small short-acting dose of a therapeutic gas, for purposes such as mild or moderate sedation. There remains a need for a device and method to quickly and painlessly administer or to have an individual self-administer a short-acting therapeutic agent to a human or mammal experiencing distress or other undesirable symptoms. The delivery needs to be easy to administer without requiring the patient to synchronize their breathing with the delivery device (the way asthma inhalers do), so that it may be used even on involuntary recipients or those who are hyperventilating. The delivery device needs to be safe so that it is not inadvertently administered. It needs to be in a delivery system that enables effective flow and volume control.

In accordance with the present invention, devices and methods are disclosed for delivering an immediate mild to moderate therapeutic agent to a human or mammal in distress.

An objective of the disclosure is a device and method for immediate and painless treatment of undesirable symptoms.

An objective of the disclosure is a device and method for licensed professionals in a variety of settings to quickly, safely, and easily calm, sedate, increase pain tolerance, or provide mild to moderate anesthesia to combative, agitated, or nervous persons or mammals.

An objective of the disclosure is a device and method to enable a person to self-administer a small dose of a fast-acting therapeutic agent in a variety of settings.

An objective of the disclosure is a device and method for administering a therapeutic agent when oral, intramuscular, intravenous, suppositories, or other forms of administration are difficult or impractical.

An objective of the disclosure is a device for delivery of a therapeutic gas where the person need not synchronize their breathing with the device's delivery.

An objective of the disclosure is a portable and handheld device capable of delivering a fast-acting therapeutic agent.

An objective of the disclosure is a portable hand held device for the delivery of a therapeutic gas, the device comprising: a gas cylinder holding a predetermined amount of compressed therapeutic gas for individual use; the gas cylinder protected by a handheld insulated housing and further having at its top end a nozzle outlet in communication with a ball valve assembly comprising a spring, a ball valve and a push pin connected to a compression trigger, such that, upon compression of the trigger, the gas flows upward through the device and emits out from the nozzle outlet.

An objective of the disclosure is a portable handheld device for holding and delivering a therapeutic gas, the device comprising: a handheld insulated housing capable of holding a cylinder of therapeutic gas, the housing having at its top end a nozzle outlet and further having a ball valve assembly in communication with a lance for penetrating a seal on the cylinder, such that when a compression trigger is compressed following release of a safety lock, an individual dose of gas flows upward through the device and emits out through the nozzle outlet.

An objective of the disclosure is a portable handheld gas delivery device where one may easily adjust the concentration of gas the patient receives.

Other advantages of the present invention will become apparent from the following descriptions, taken in connection with the accompanying figures, wherein, by way of illustration and example, several exemplary embodiments of the present invention are disclosed.

SUMMARY

A nozzle apparatus for dispensing an adjustable combination of gas, having a nozzle outlet adjustably combined with a delivery component. The nozzle outlet may have a groove for receiving a roll pin; and an inner lumen comprising a cylindrical shaft having a diameter between 5/1000ths and 20/1000ths of an inch. The delivery component configured to receive air from the nozzle outlet, may have a first circular ambient air hole having a diameter, and a second circular ambient air hole having the same diameter as the first ambient air hole, and a removable plugging device covering the second circular ambient air hole. The delivery component may be adjustable in orientation with respect to the nozzle outlet, and may be adjustable to vary a concentration of therapeutic gas delivered to a patient.

BRIEF DESCRIPTION OF THE DRAWINGS

The figures constitute a part of this specification and include exemplary embodiments to the invention, which may be embodied in various forms. It is to be understood that in some instances various aspects of the invention may be shown exaggerated or enlarged to facilitate an understanding of the invention. To enable more thorough understanding of the features and advantages of the present invention, reference is now made to the detailed description of the invention along with the accompanying figures in which.

DETAILED DESCRIPTION

Figure 1:
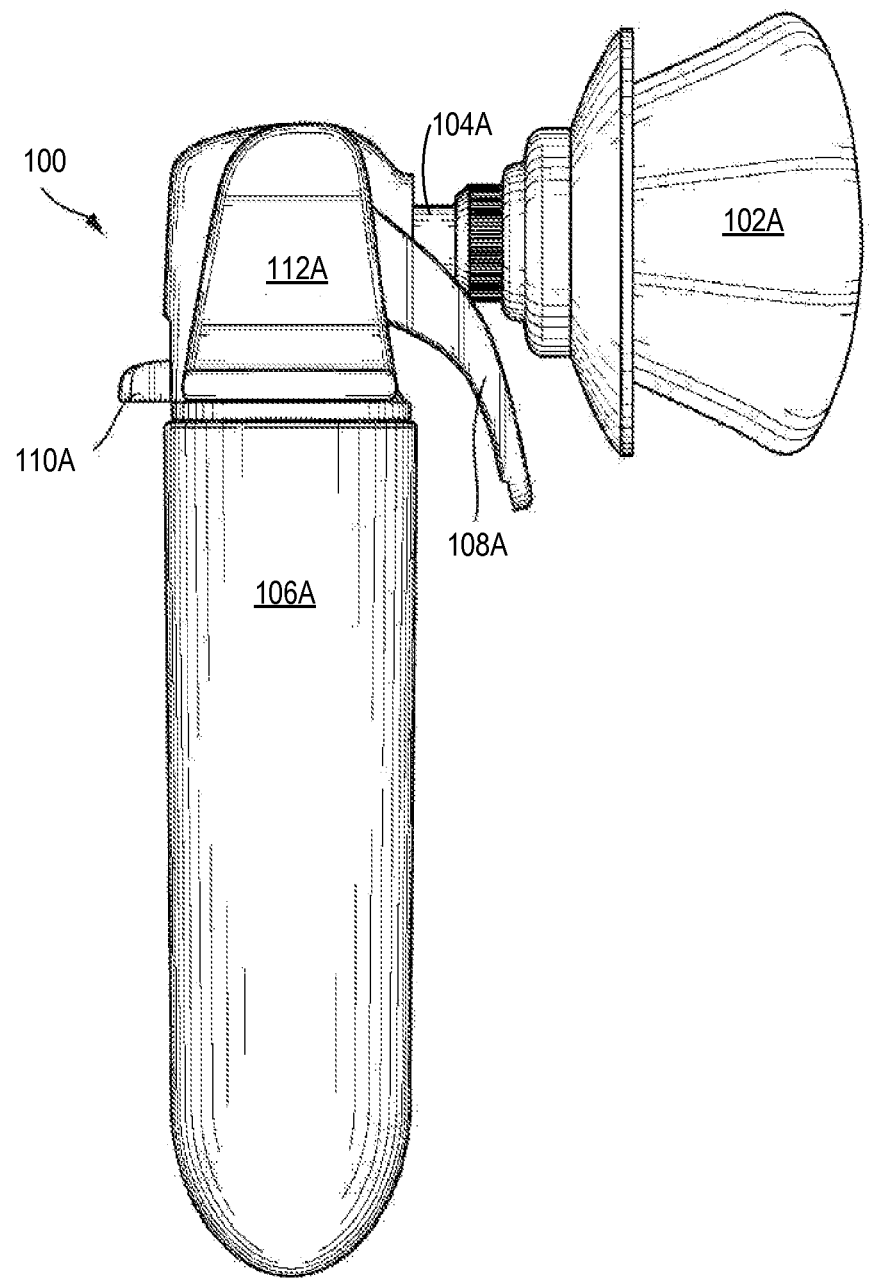
FIG. 1 is a side view of a first gas delivery device in accordance with an exemplary embodiment of the present invention.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

There are a multitude of settings where it would be extremely advantageous to be able to quickly and painlessly achieve a mild to moderate level of sedation, anesthesia, pain relief, or increased pain tolerance in an agitated or uncomfortable human or animal. In most of these situations the need is only for a short period of time and only a mild to moderate effect would be necessary. A few examples of such settings include veterinarian offices, specialty clinics, minor emergency centers, dentist offices, tattoo parlors, outpatient surgery centers, and psychiatric hospitals. In each of these scenarios, the patient may be mildly nervous and anxious. The ability to administer to them a fast-acting mild or moderate sedative just to get them through an examination, a short procedure, or a pre-anesthesia period would be very beneficial, especially if the sedative could be administered in such a way that it is painless, takes effect almost immediately, wears off relatively quickly, and has limited side effects. Known sedatives or mild pain relievers in the oral, intramuscular, intravenous, or other forms are typically prescription only and, for safety reasons, are typically not available for administration by non-medical licensed professionals such as police officers, security officers, tattoo artists, or school nurses. A safer form of sedative or calming agent that could be administered by such professionals would be of great use.

Police officers often use Tasers® to subdue agitated persons and there can be a risk of injury or damage from use of these weapons. The disclosed device and method would be effective for those persons who are mildly agitated and need to be calmed but do not require the level of violent intervention provided by a Taser®. Police officers may also find this device useful for people involved in car accidents or other traumatic scenarios.

As another example, there are times when patients in an outpatient medical setting such as a minor emergency center or clinic (for example, dermatology, plastic surgery, cardiac cath labs for stent placement, gynecology, urology, gastroenterology, addiction centers, psychiatric wards, hospice care, midwives, dentist offices, prisons, pediatrics clinics, hair removal, tattoo placement or removal (including beauty and facial tattooing on eyes and lips)), need a procedure that, due to the minor nature of the procedure or due to time limitations would not warrant the use of prescription drugs or general anesthesia, yet the patient may still feel fear, anxiety, pain or nervousness. Many patients are fearful of needles. The administration of one of the disclosed devices and methods would help them relax enough to allow the procedure and to better tolerate any necessary aspects such as the administration of local numbing medicine through painful needle injections. Another potential application is in to package and sell the device with first aid or minor emergency kits. The military would undoubtedly find the device extremely useful in a variety of settings including on the field and in combat. To be able to quickly calm and/or ease pain of a wounded or highly anxious soldier, without the need for needles or pills, could be of great value.

There are also times when persons are undergoing a stressful experience and would desire to self-administer a mild to moderate sedative or anesthesia for an effect that is short-acting. Examples include when flying in a plane, preparing to give a speech, or prior to any sort of stressful encounter.

In such scenarios, the self-administering patient would typically want the effects to be short in duration so that they could be at full mental and physical alertness shortly thereafter. Taking a pill in such a situation is risky because the patient never knows how long the effects of a pill may stay in their system. Furthermore, the nature of the delivery system described herein enables the patient to control how much gas to breathe in.

Although a variety of potential therapeutic gases and combinations of gases could be used, those primarily known for therapeutic purposes include nitrous oxide, xenon, helium, and carbon dioxide. Other agents and medications are currently being evaluated by scientists for reformulation into a therapeutic gas delivery system, including drugs for diabetes, heart conditions, panic attacks, and other conditions. This same device can deliver different gases for other applications like these as well, and could even potentially be used to deliver gases including but not limited to halothane, enflurane, isoflurane, desflurane, sevoflurane, methoryflurane, diethylether, chloroform, cyclopropane, trichloroethylene, and fluroxene.

Nitrous oxide is an example of a therapeutic gas that is used in small doses with the disclosed delivery system to cause a mild or moderate sedative or anesthetic effect. Although use in medical type settings has already been discussed, nitrous oxide gas could also be used by those desiring to combat sleeplessness, such as truckers at truck stops or patrons of hotels who are often "wired" from long hours of travel. The administration of the small amount of nitrous oxide would calm them enough to allow them to relax and sleep, without causing the "morning hangover" so common with traditional oral sleep aids.

The delivery apparatus for delivery of the described therapeutic gases is critical. The delivery apparatus should be safe so that it is not inadvertently administered, it should be small and portable, it should have a reasonable price point, and it should be capable of easy administration to either a voluntary or involuntary human or mammal patient.

As the methods and devices disclosed herein may undergo Food and Drug Administration approval for its application, the disclosed delivery devices are carefully designed to meet the application needs described in a safe and efficacious manner. The delivery devices can be sterilized and can deliver a limited maximum amount. The gas may be emitted in a controlled and slow fashion so that the user may easily control the amount delivered. Different sizes of outlets may be used depending on how fast the user wishes the gas to be dispensed or the type of gas in the cylinder. It may utilize a mouthpiece or mask delivery component, which when used in combination with the slow continuous flow design, may result in a multitude of advantages over known "puff" or "blast" type inhalers such as those used for asthma patients. With a "puff" type delivery system, the patient must synchronize their breathing with the device in order to effectively breathe in the medicine. They cannot adjust the volume delivered because the puff amount will be the same each time. "Puff" type devices are difficult to use on involuntary patients due to the need for an open mouth, synchronization of the breathing, and because the patient can just turn their head as the puff is being delivered.

Referring to FIG. 1, depicted is a side view of a first gas delivery device 100 with a mask 102A for delivery of the compressed gas to the mouth and nose. Gas emits from the nozzle outlet 104A into the mask 102A.

The nozzle outlet 104A ends in a nozzle cap. The mask 102A may be removably affixed to the device by sliding the mask 102A over the nozzle cap. FIG. 1 further shows a protective housing 106A within which is located a cylinder of compressed therapeutic gas, a compression trigger 108A to deploy the gas from the cylinder into the mask 102A, and a locking mechanism 110A for preventing unintended deployment of gas. A cover cap 112A is shown as well which protects certain of the components.

Gas delivery device 100 incorporates a gas cylinder in protective housing 106A. The gas cylinder holds a predetermined amount of compressed therapeutic gas. The housing 106A should be insulated to protect the user from the cold of the cylinder which occurs as a result of the compressed gas being released.

Gas delivery device 100 incorporates safety locking mechanism 110A as a safety feature, preventing unintentional administration. Locking mechanism 110A places an obstruction, such as, but not limited to, a spacing member in a position under compression trigger 108A so as to make compression trigger 108A unable to release the gas. Locking mechanism 110A holding compression trigger 108A firmly up causes locking mechanism 110A to lock in place.

Gas delivery device 100 incorporates mask 102A as a delivery component to make administration easier and more efficient. A mouthpiece may be used as a delivery component in place of mask 102A, as will be shown with reference to FIG. 4.

A mask delivery component may cover just the patient's mouth, or the patient's mouth and nose. The delivery component, whether a mask or a mouthpiece, may be disposable. Housing 106A, the canister cover, may accommodate different gas cylinders such as small ones of 8 grams up to larger multi-unit doses cylinders holding up to 24 grams.

Figure 2:
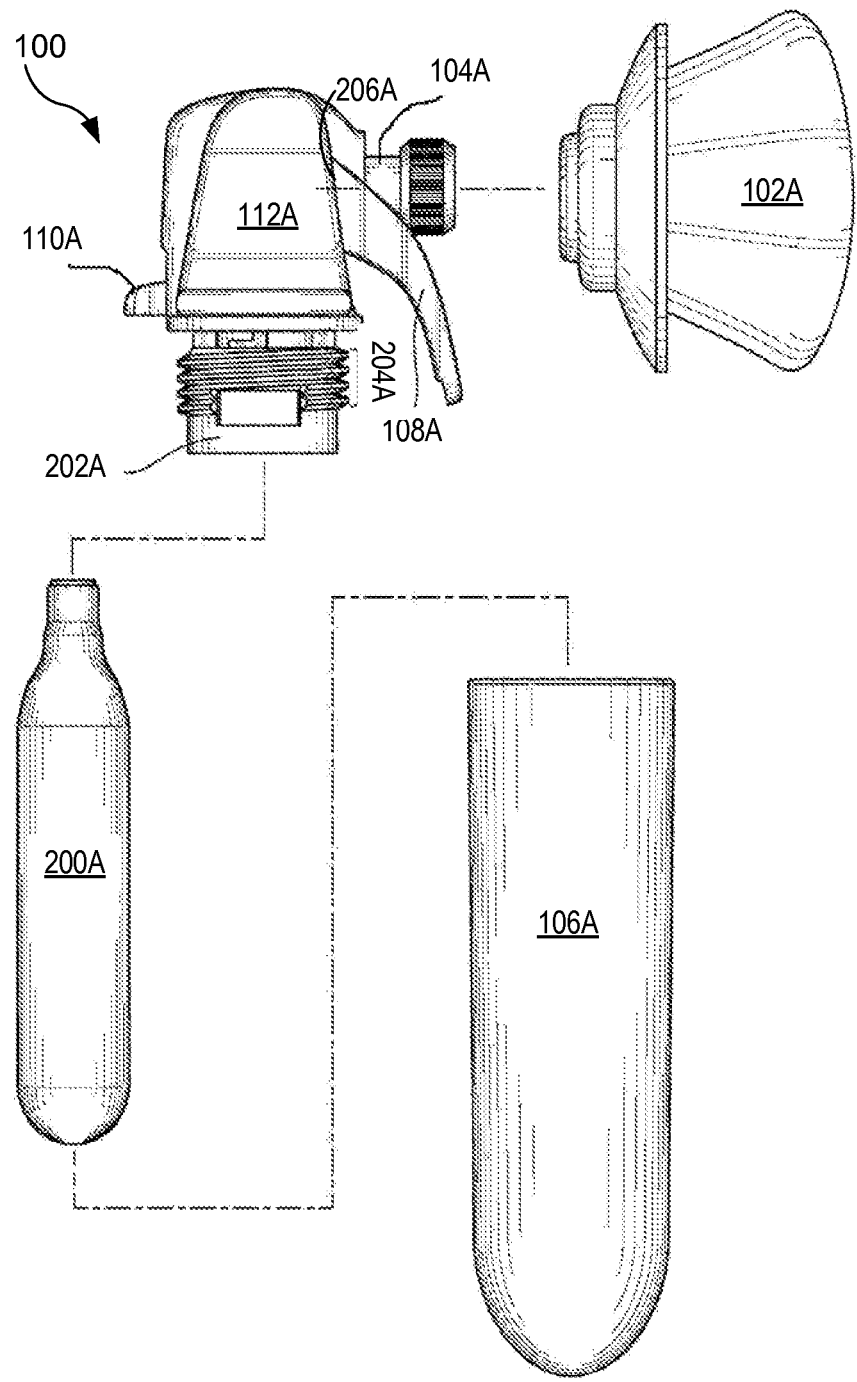
FIG. 2 is an exploded view of the first gas delivery device.

Referring to FIG. 2, depicted is an exploded view of the components of the device 100. The cylinder 200A is shown as is the housing 106A which holds and protects the cylinder and similarly protects the user's hands from the cold cylinder. The cylinder 200A threads onto the head 202A of the device 100 while the housing 106A threads over the exterior threads 204A of the head 202A. The compression trigger 108A is seen as well as the locking mechanism 110A. When the cylinder 200A is empty, housing 106A can be unthreaded from head 202A, the empty cylinder 200A can be replaced with a full cylinder, and housing 106A can be again threaded onto head 202A.

Also pictured in FIG. 2 is the nozzle outlet 104A. Inside nozzle outlet 104A, in a portion covered by cover cap 112A in FIG. 2, is an inner lumen 206A running through at least a portion of the length of nozzle outlet 104A. In an embodiment, the inner lumen 206A may be between 0.05 and 0.5 inches long. The inner lumen 206A may be a cylindrical shaft with a diameter that controls the gas flow. In other words, the diameter of the inner lumen 206A is a bottleneck which limits the rate the gas flows. The diameter of the inner lumen 206A is important because it prevents the gas from flowing too quickly or too slowly. Gas flowing too quickly may cause formation of ice crystals and overdosing, while gas flowing too slowly may cause underdosing. The diameter of the inner lumen 206A is preferably less than $5/1000$ths of an inch but more than $1/1000$ths of an inch, in order to ensure a continuous but slow flow of gas. More preferably, the diameter of the inner lumen 206A is between $20/1000$ths of an inch and $5/1000$ths of an inch. Most preferably, the diameter of the inner lumen 206A is $11/1000$ths of an inch. The diameter of the inner lumen 206A may also be less than $5/1000$s of an inch and more than $1/1000$s of an inch.

Figure 3:
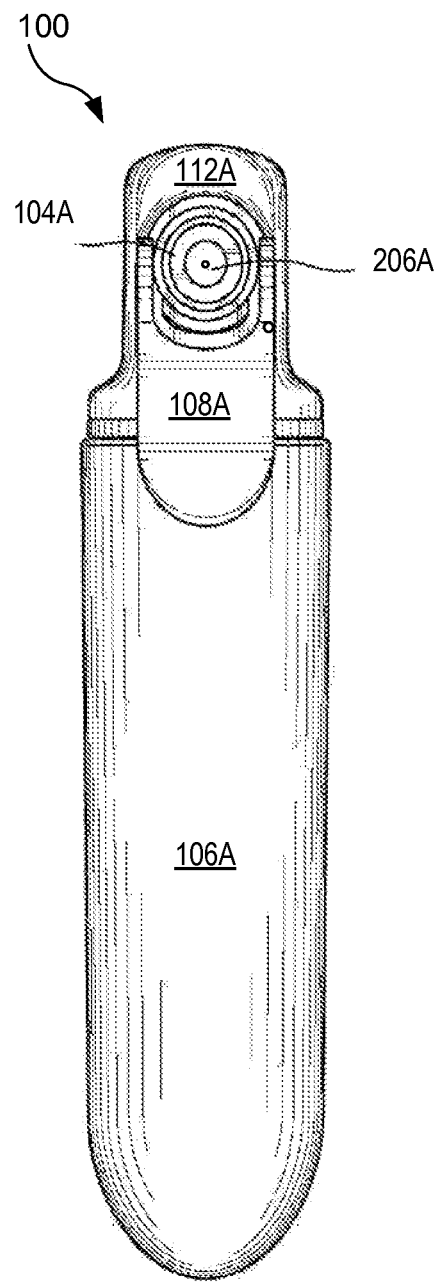
FIG. 3 is a front close up view of the first gas delivery device.

FIG. 3 is a close-up front view of the device 100, showing more clearly the nozzle outlet 104A and the inner lumen 206A from which the gas emits into the mask or mouthpiece. In FIG. 3, no delivery component is affixed to the device 100. Also shown is the front of the trigger 108A, as well as the front top of the cover cap 112A and the housing 106A.

Referring to FIGS. 1-3, to dispense the gas, the user turns safety locking mechanism 110A off and compresses compression trigger 108A. Nozzle outlet 104A may be of different sizes depending on the type of gas and the desired rate of continuous flow, but in most applications the desired outcome is that the user will compress the trigger 108A and the patient will receive a slow and steady predetermined rate of gas flow through a mask or mouthpiece delivery component. As the cylinders are small and meant for individual use, a patient will not be able to "overdose" or take in unsafe amounts as the cylinder 200A would deplete before that could happen.

Figure 4:
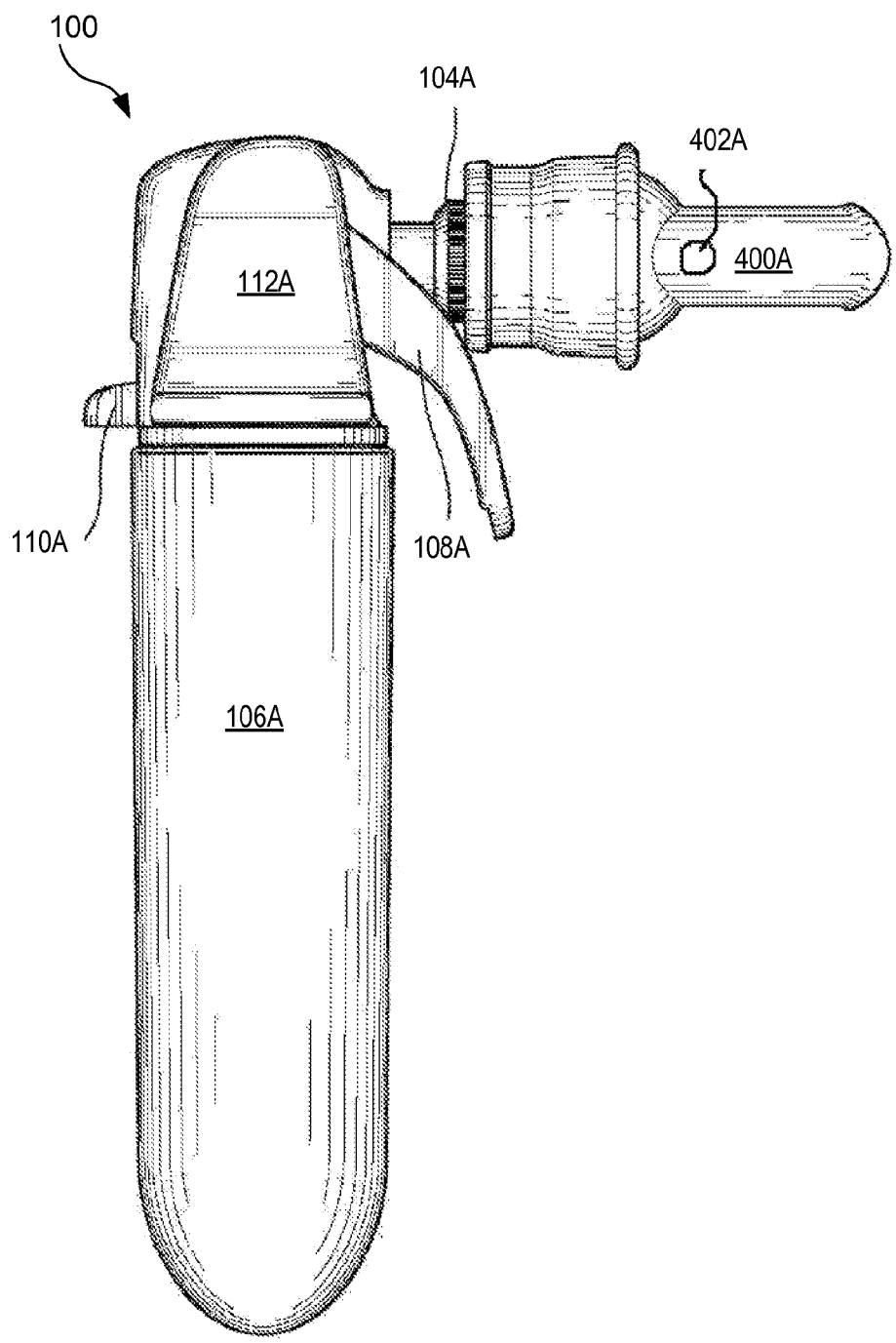
FIG. 4 is a side view of the first gas delivery device with a mouthpiece.

FIG. 4 is a side view of the device 100 having the same features except with a mouthpiece 400A as the delivery component rather than the mask shown previously. Also shown from the side is the nozzle outlet 104A again. The mouthpiece 400A preferably is removably affixed to the nozzle outlet 104A by sliding onto the nozzle cap of the nozzle outlet 104A. Mouthpiece 400A comprises a tube which is placed inside the patient's mouth, from which the patient inhales.

Mouthpiece 400A may have one or more ambient air holes 402A in it. A mask delivery component may likewise have ambient air holes in it. When the user breathes in, the user's inhalation pulls ambient air into the delivery component through the ambient air holes. The concentrated gas is naturally mixed with the ambient air, and the patient inhales a diluted concentration of the gas. The size of the ambient air holes relative to the size of the inner lumen of the nozzle outlet determines the amount of dilution.

For example, a gas cylinder holds 100% nitrous oxide and the nozzle has a particular inner diameter. With no ambient air holes in the delivery component, the concentration of gas is approximately 100%. A delivery component having ambient air holes of a certain diameter may be employed such that the user, upon inhalation, receives a nitrous/oxide concentration of less than 100%, the holes being specifically manufactured to correspond with the desired concentrations. Desirable percentages will vary depending on type of gas and use. Exemplary desired concentrations may be 50% or 70%.

With a removably affixed delivery component, by changing the delivery component one may change the concentration of gas inhaled. For example, one may replace a mouthpiece sized to dilute gas in the cylinder to 50% with a mouthpiece sized to dilute gas in the cylinder to 70%. Other than the different delivery component, the rest of the device may be the same, including the gas cylinder and nozzle. Thus, a single gas cylinder may be used to provide varying concentrations of gas.

Figure 5:
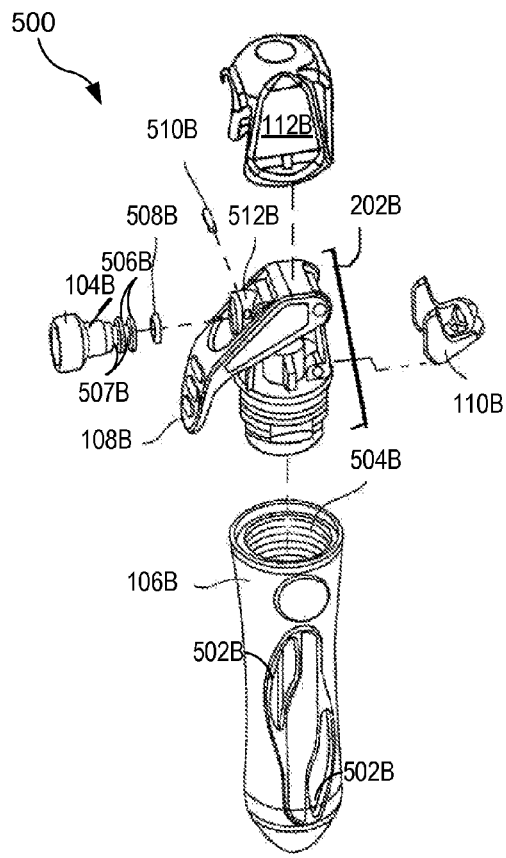
FIG. 5 is a perspective exploded view of a second gas delivery device in accordance with an exemplary embodiment of the present invention.

FIG. 5 is an exploded view of the components of a second gas delivery device 500. Second gas delivery device 500 is substantially identical to the first gas delivery device except for differences mentioned or shown. Parts on the first and second gas delivery devices that share the same part numbers, such as housing 106A and housing 106B, are identical in relevant aspects except for differences mentioned or shown.

Housing 106B has open or transparent viewing windows 502B. Any gas cylinder in housing 106B is visible through viewing windows 502B. Through viewing windows 502B, a user can quickly verify whether or not a gas cylinder is loaded in housing 106B. Housing 106B has interior threads 504B. Into the housing 106B threads the head 202B of the device 500, atop which is the compression trigger 108B.

On the front of the head 202B are shown components including the nozzle outlet 104B. Nozzle outlet 104B may be preferably 1.32 inches (33.5 mm) long. Nozzle outlet 104B may also be preferably between 1.02 inches (26.0 mm) and 1.62 inches (41.2 mm) long. The portion of nozzle outlet 104B outside head 202B may preferably be 0.95 inches (24.2 mm) long. The portion of nozzle outlet 104B outside head 202B may also be preferably between 0.65 inches (16.6 mm) and 1.25 inches (31.8 mm) long.

The end of nozzle outlet 104B which enters head 202B has two flanges 506B. Flanges 506B, together with the wider front end of nozzle outlet 104B, form two grooves 507B. The rear groove 507B is formed by the front flange 506B and the rear flange 506B. O-rings 508B fit into the rear groove 507B before the nozzle outlet 104B slides into place in the head 202B. The o-rings 508B seal the connection between nozzle outlet 104B and head 202B, preventing gas from escaping out to the sides and forcing the gas into the inner lumen of the nozzle outlet 104B.

The front groove 507B is formed by the wider front end of nozzle outlet 104B and the front flange 506B. Roll pin 510B passes through roll pin hole 512B, through the front groove 507B, and through another roll pin hole (not shown) on the other side of head 202B. Roll pin 510B secures the nozzle outlet 104B to the head 202B and allows the nozzle outlet 104B, and any attached delivery component, to be rotatable 360 degrees. An attached delivery component may therefore be inverted relative to the housing 106B. Roll pin 510B may be composed of stainless steel.

Roll pin 510B is important because gas cylinder 200B, and consequently housing 106B and head 202B, must be kept upright and nearly vertical for proper gas flow. Otherwise, gas flowing into nozzle outlet 104B tends to form ice crystals. Roll pin 510B permits the delivery component to rotate to a position convenient for the patient while the gas cylinder is kept upright. For example, while lying down, a patient may turn the patient's head while inhaling from a mask or mouthpiece.

On the back of the head 202B is located the safety locking mechanism 110B. The head 202B threads into the housing 106B and the cover 112B fits over the head 202B, protecting the internal components of the head 202B.

Figure 6:
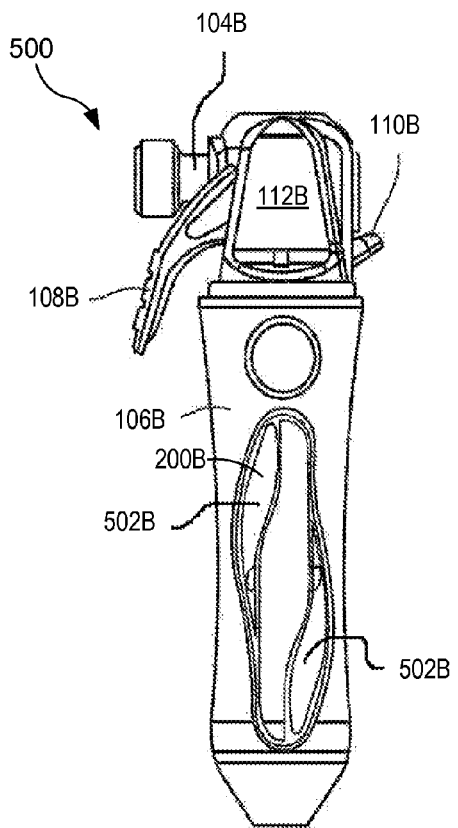
FIG. 6 is a side view of the second gas delivery device.

FIG. 6 is a side view of second device 500, showing the FIG. 5 components as they appear assembled with a gas cylinder 200B. The housing 106B is pictured. Housing 106B houses the compressed gas cylinder 200B which is visible through open or transparent viewing windows 502B constructed into the housing 106B. Pictured above the housing 106B is the head cover 112B from the front of which emerges the trigger 108B and, superior to the trigger 108B, emerges the nozzle outlet 104B. From the back side of the head 202B emerges the safety locking mechanism 110B.

Figure 7:
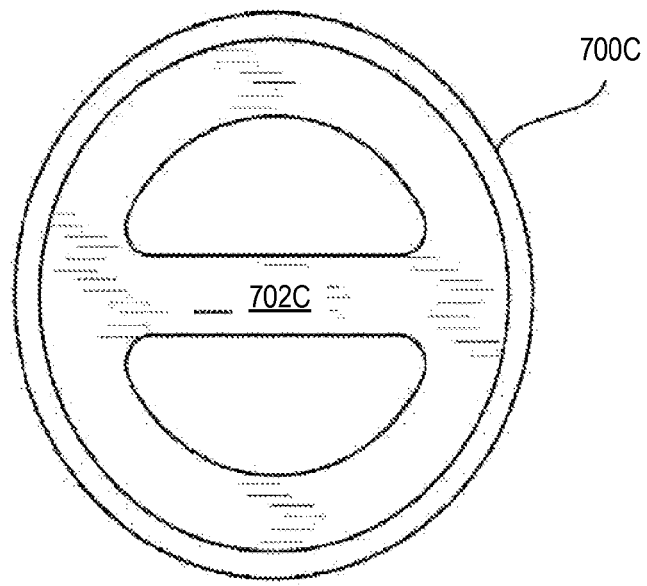
FIG. 7 is a front view of a nozzle cap of a third gas delivery device in accordance with an exemplary embodiment of the present invention.

Pictured in FIG. 7 is a close up front view of a nozzle cap 700C for a third gas delivery device. In the third gas delivery device, nozzle cap 700C is the end-piece of the nozzle outlet. Nozzle cap 700C may have interior threads and the nozzle outlet may have exterior threads. Nozzle cap 700C may screw over exterior threads of the nozzle outlet. Nozzle cap 700C may be removable from the nozzle outlet or may be glued in place.

The front end of the nozzle cap 700C comprises a safety plate 702C. Safety plate 702C is a novel safety feature that acts as a debris filter. Safety plate 702C protects the patient from unwanted debris, such as ice, from entering the user's mouth upon use. Compressed gas, when released, generates cold, sometimes forming ice crystals. Upon compression of the trigger, the gas, and any ice crystals, may flow through the nozzle outlet. The safety plate 702C will prevent any pieces of ice from exiting the nozzle.

Different sizes of nozzle caps are possible. A nozzle cap may have a thicker or thinner width to fit delivery components that receive gas through holes of different sizes. Safety plates may also come in different sizes, with different shapes of holes to permit the gas to pass while filtering out debris. Safety plate 702C has two lumen-shaped holes for the gas, as shown in FIG. 7.

Figure 8:
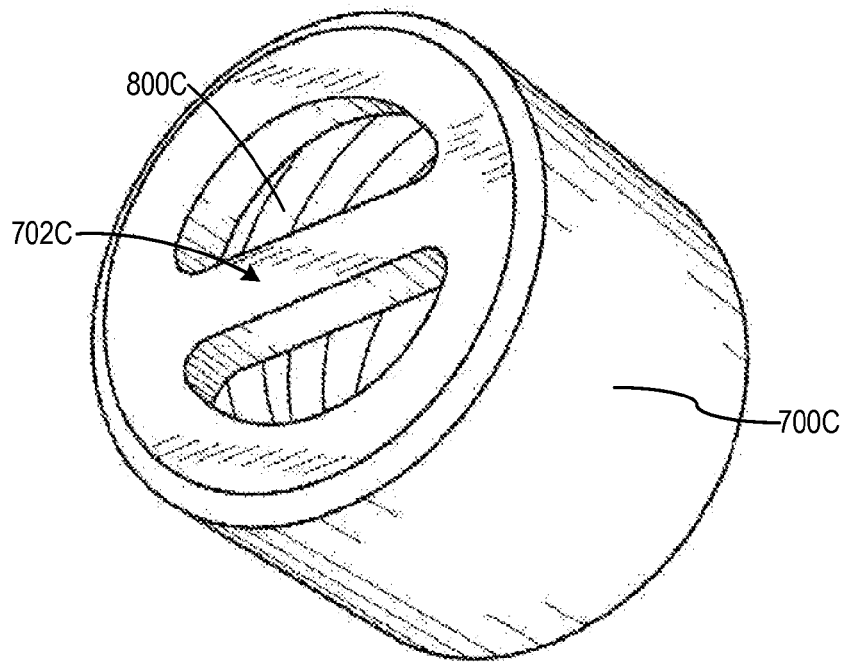
FIG. 8 is a perspective view of the nozzle cap of the third gas delivery device.

FIG. 8 is a side perspective view of the nozzle cap 700C, again showing the safety plate 702C. Safety plate 702C is positioned on the front end of the nozzle outlet when nozzle cap 700C is affixed to the nozzle outlet. Interior threads 800B thread over exterior threads of the nozzle outlet.

Figure 9:
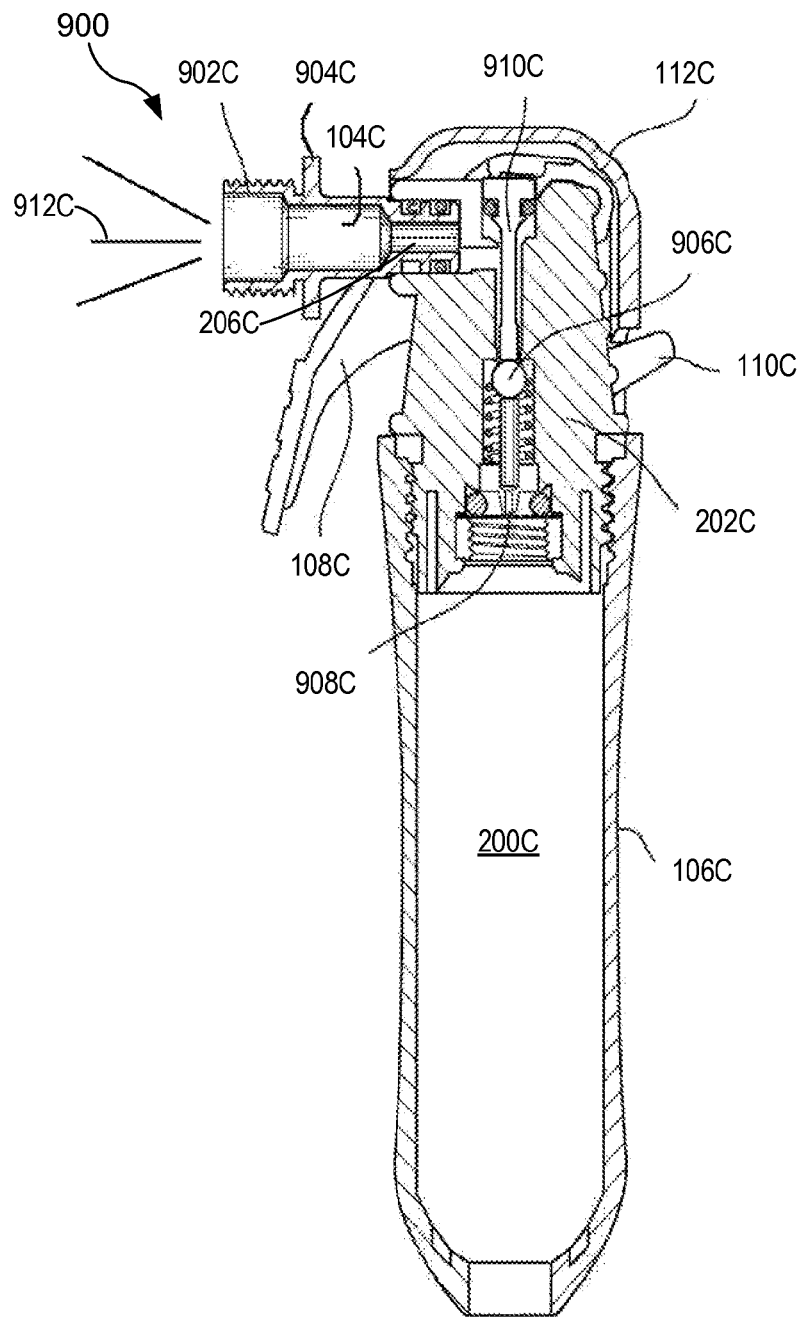
FIG. 9 is a cross sectional view showing the internal assembled components of the third gas delivery device.

FIG. 9 is a cross sectional view of the third device 900 showing the internal assembled components and the special design which enables the slow continuous flow of the predetermined amount of gas upon depression of the trigger. Third gas delivery device 900 is substantially identical to the second gas delivery device except for differences mentioned or shown. Parts on the second and third gas delivery devices that share the same part numbers, such as housing 106B and housing 106C, are identical in relevant aspects except for differences mentioned or shown. The preferable lengths of nozzle outlet 104C are the same as the preferable lengths previously described for nozzle outlet 104B.

Nozzle cap 700C is removed from nozzle outlet 104C in FIG. 9, revealing nozzle outlet exterior threads 902C. Third device 900 has retaining lip 904C, a flange which stops the mask or mouthpiece delivery component from impeding the trigger 108C. A delivery component may be attached to third device 900 by sliding the delivery component until it is flush against retaining lip 904C.

The housing 106C is shown surrounding the gas cylinder 200C. The top of the gas cylinder 200C may be unthreaded or threaded and is placed inside or threaded into the base of the head 202C. The top of the cylinder 200C is sealed into the base of the head 202C prior to use.

The gas cylinder 200C is activated when the housing 106C with cylinder 200C is torqued onto the base of the head 202C which is in communication with a ball and spring ball valve 906C which is further in communication with the lance 908C. The compressed gas from the cylinder 200C flows through the lance 908C when the cylinder 200C is punctured. The gas is trapped in the head 202C behind the ball valve 906C.

When the trigger 108C is compressed, the push pin 910C pushes on the ball valve 906C, opening the valve 906C and allowing gas 912C to flow up and through the nozzle outlet 104C. Inner lumen 206C inside nozzle outlet 104C limits the rate gas 912C can flow. In an embodiment, the inner lumen 206C may be between 0.05 and 0.5 inches long. Gas 912C then passes through the attached nozzle cap, including through the safety plate, which filters gas 912C for debris, and into the delivery component to be inhaled. The preferable dimensions of inner lumen 206C are the same as the preferable dimensions of the inner lumen 206A of the first gas delivery device.

Figure 10:
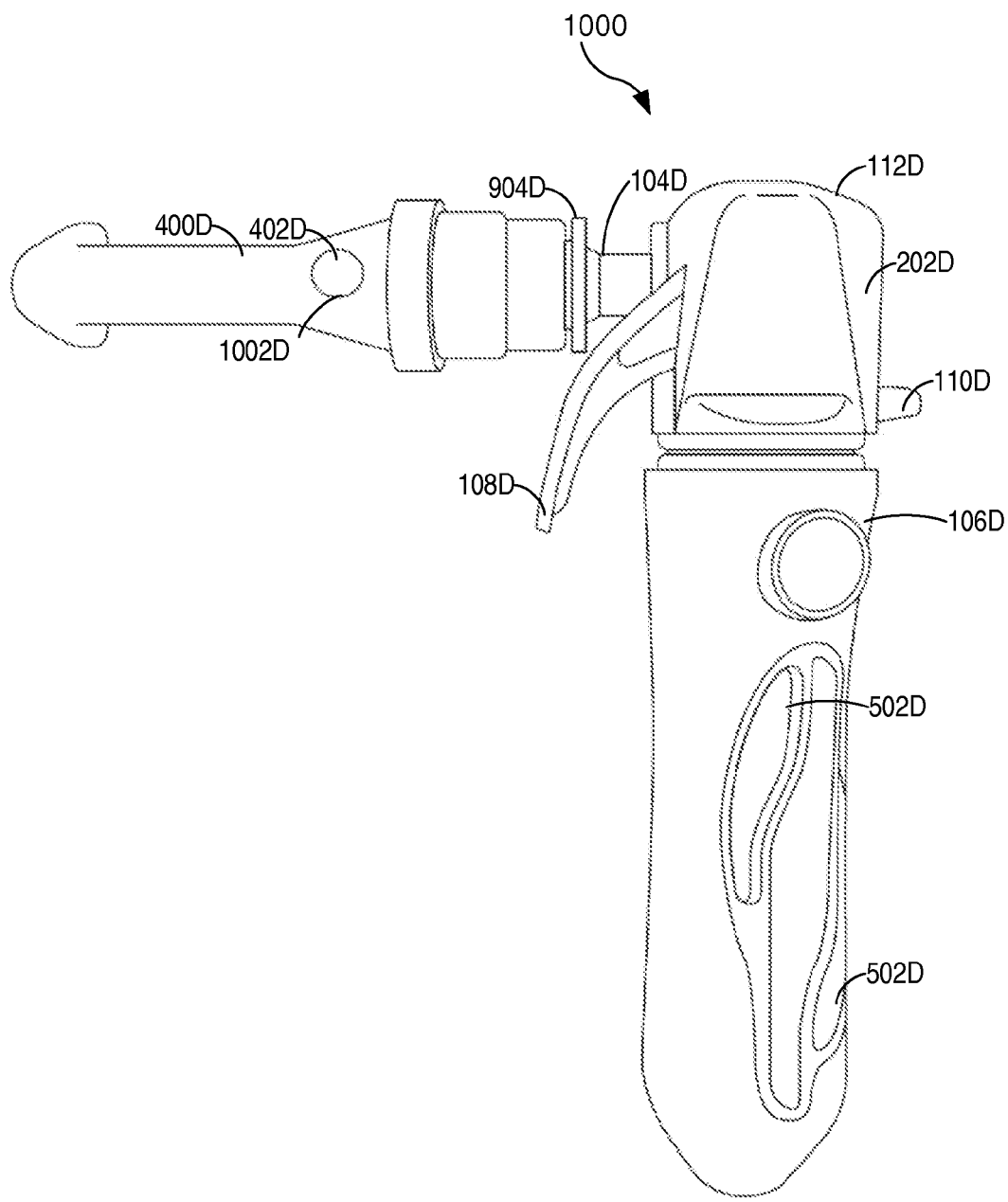
FIG. 10 is a side view of a fourth gas delivery device with a mouthpiece affixed in accordance with an exemplary embodiment of the present invention.

FIG. 10 is a side view of a fourth gas delivery device 1000 with an attached mouthpiece 400D. Mouthpiece 400D, like the previously shown mouthpiece 200A, comprises a tube which a patient may place the patient's lips around, and from which the patient may inhale. Fourth gas delivery device 1000 is substantially identical to the third gas delivery device except for differences mentioned or shown. Parts on the third and fourth gas delivery devices that share the same part numbers, such as housing 106C and housing 106D, are substantially identical except for differences mentioned or shown. The preferable lengths of nozzle outlet 104D are the same as the preferable lengths previously described for nozzle outlet 104B.

Fourth gas delivery device 1000 differs from the third gas delivery device only in the flow of the gas after it reaches nozzle outlet 104D. Prior to this point, the parts of fourth gas delivery device 1000 are and function the same as the parts of the third gas delivery device, and need not be explained again. Housing 106D, compression trigger 108D, locking mechanism 110D, cover cap 112D, cylinder 200D (removed from the device 1000 in FIG. 10), head 202D, viewing windows 502D, and retaining lip 904D are nonetheless shown for reference. A patient lying on the patient's back would turn the patient's head to the side to breathe from mouthpiece 400D. Device 1000 would remain upright.

After leaving nozzle outlet 104D, the gas may pass through an optional particle filter and a nozzle cap. The fourth device's particle filter and nozzle cap will be explained further with reference to FIGS. 11-12. The gas then enters mouthpiece 400D.

Mouthpiece 400D has two circular ambient air holes 402D, one on each side of mouthpiece 400D. Each ambient air hole 402D preferably has a diameter of 0.28 inches or 7.1 mm.

More generally, ambient air hole diameters in the range of 0.18 inches to 0.38 inches may be suitable.

Initially, one ambient air hole 402D is covered with a removable sticker 1002D. With the preferred ambient air hole diameter and an inner lumen diameter of $^{11}/_{1000}$ths of an inch, a patient inhaling from mouthpiece 400D will inhale gas with a concentration of approximately 65-70% of the concentration of gas in cylinder 200D (not shown).

In the second and third gas delivery devices, as described above, one may vary the concentration of gas inhaled by using a different delivery component. In fourth gas delivery device 1000, a removable plugging device such as removable sticker 1002D may offer a mechanism for varying the concentration of gas inhaled without replacing mouthpiece 400D. By removing removable sticker 1002D, a user may decrease the concentration of gas inhaled to approximately 50% of the concentration of gas in cylinder 200D. The removal of sticker 1002D permits air to enter through the uncovered ambient air hole 402D. Thus, removal of sticker 1002D decreases the concentration of gas inhaled.

In some cases, one may wish to increase the concentration of gas inhaled to approximately 100%. A user may leave one ambient air hole 402D covered by sticker 1002D and cover the other ambient air hole 402D, such as with the user's finger. Alternately, device 1000 may be provided with plugging devices, such as stickers 1002D, covering both ambient air holes. With both ambient air holes 402D covered, the concentration of gas inhaled will be approximately that of the concentration of gas in cylinder 200D.

Delivery of the proper concentration depends on both the size of the ambient air holes in the delivery component and the size of the inner lumen in the nozzle outlet. Thus, the removable stickers or other plugging devices on the delivery component may be sized with the assumption the delivery component will be used with a nozzle outlet inner lumen of a particular size.

In more general terms, a delivery component may have multiple ambient air holes of varying sizes, with some or all ambient air holes covered by removable stickers, covers, or other removable plugging devices. With such a delivery component, a user may remove stickers or cover ambient air holes to configure the delivery component for diluting gas inhaled to a desired concentration. Thus, with only a single delivery component, one may choose among multiple different concentrations of gas inhaled, for example 40%, 35%, or another dilution between 1% and 100%.

Figure 11:
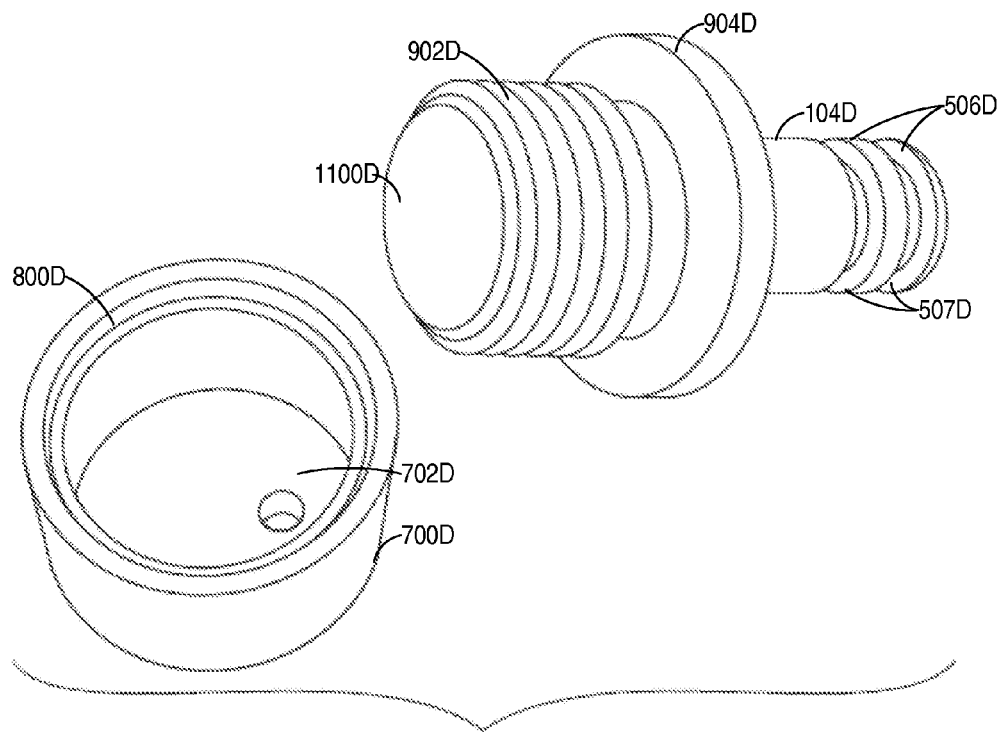
FIG. 11 depicts the interiors of the nozzle outlet and nozzle cap of the fourth gas delivery device when the two parts are disassembled.
Figure 12:
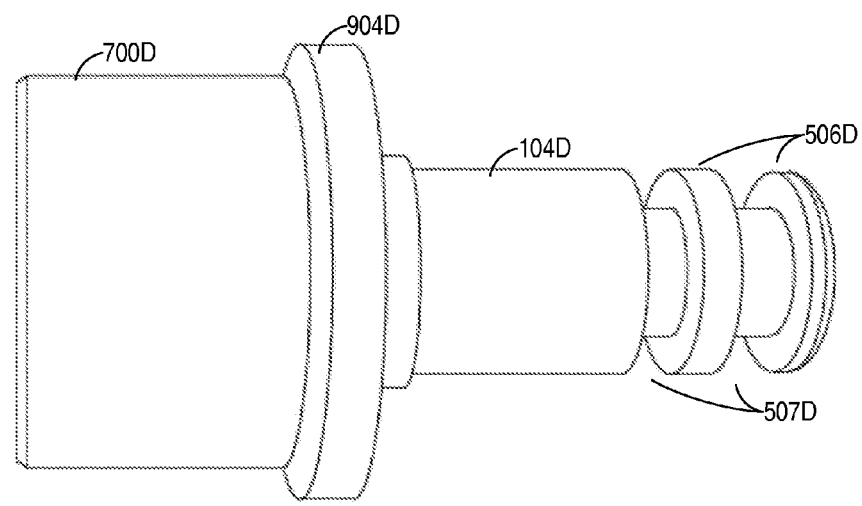
FIG. 12 is a side view of the nozzle cap and nozzle outlet of the fourth gas delivery device when the two parts are assembled.

Referring to FIG. 11, depicted are the interiors of nozzle outlet 104D and nozzle cap 700D when the two parts are disassembled. Referring to FIG. 12, depicted is a side view of nozzle outlet 104D and nozzle cap 700D when assembled. As in the third gas delivery device, the interior threads 800D of nozzle cap 700D thread over exterior threads 902D of nozzle outlet 104D. As in the second and third gas delivery devices, nozzle outlet 104D has two flanges 506D. One or more o-rings are held in the rear groove 507D between flanges 506D, and a roll pin is held in the front groove 507D between front flange 507D and the front end of nozzle outlet 104D. Also as in the third gas delivery device, retaining lip 904D prevents the delivery component from impeding compression trigger 108D.

Referring to FIG. 11, replaceable particle filter 1100D may be inside nozzle outlet 104D. Replaceable particle filter 1100D is optional and device 100D may function without it. When in use, replaceable particle filter 1100D filters microscopic impurities and debris from gas leaving nozzle outlet 104D.

Nozzle cap 700D and its safety plate 702D hold replaceable particle filter 1100D inside nozzle outlet 104D. Instead of the two lumen-shaped holes in the safety plate of the third gas delivery device, safety plate 700D has a single, small round hole. When replaceable particle filter 1100D is not present, safety plate 700D may filter debris from the gas like the safety plate in the third device.

Figure 13:
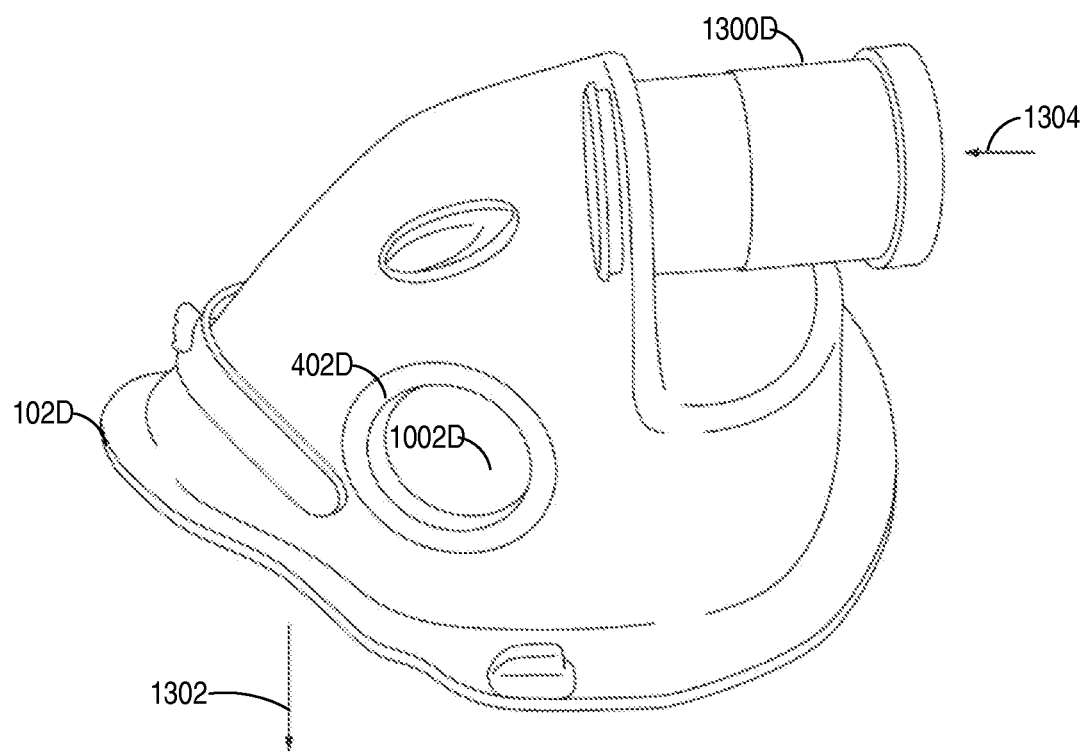
FIG. 13 is a perspective side view of a mask for the fourth gas delivery device.
Figure 14:
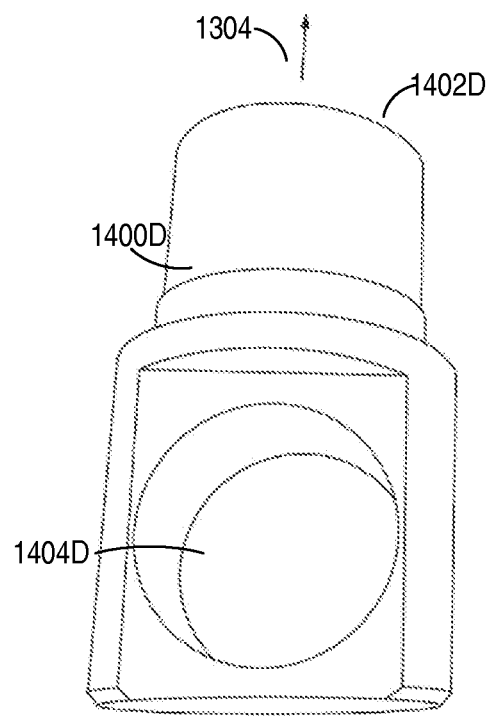
FIG. 14 is a rear view of an elbow component for the mask of the fourth gas delivery device.

Referring to FIGS. 13-14, depicted is a perspective side view of a mask 102D for the fourth gas delivery device and a rear view of associated elbow component 1400D. Like mouthpiece 400D, mask 102D may have two circular ambient air holes 402D, with one or both ambient air holes 402D covered by removable plugging devices, such as removable stickers 1002D. Ambient air holes 402D in mask 102D may preferably each have a diameter of 0.70 inches or 17.9 mm. More generally, ambient air hole diameters in the range of 0.5 inches to 0.9 inches may be suitable.

Ambient air holes 402D and sticker 1002D may serve the same function as in mouthpiece 400C. With sticker 1002D covering one ambient air hole 402D and the other ambient air hole 402D uncovered, a patient may inhale gas diluted to approximately 65-70% of the concentration of gas in the cylinder. With sticker 1002D removed, the patient may inhale gas diluted to approximately 50% of the concentration of gas in the cylinder. With both ambient air holes 402D covered, the patient may inhale gas with approximately the same concentration as the gas in the cylinder.

Together, mask 102D, elbow component 1400D, flanges 104D in the nozzle outlet, and the roll pin in the device head may allow mask 102D to rotate to a variety of positions. As mentioned above, it is important for the gas cylinder to be kept upright. The rotation of mask 102D allows a patient wearing mask 102D to move the patient's head while keeping the gas cylinder upright.

Mask 102D opens in mask opening direction 1302. The patient may inhale gas from mask 102D in mask opening direction 1302. Mask 102D has mask gas entry tube 1300D. Mask gas entry tube 1300D may be open in and receive gas from elbow component direction 1304. Elbow component direction 1304 may be perpendicular or substantially perpendicular to mask opening direction 1302. A substantially perpendicular direction is within 20 degrees of perpendicular, between 70 and 110 degrees.

Mask gas entry tube 1300D may receive gas exit tube 1402D of elbow component 1400D. Elbow component 1400D also has opening 1404D, which receives gas from nozzle outlet 104C. Mask gas entry tube 1300D may rotate about the length of gas exit tube 1402D.

Figure 15:
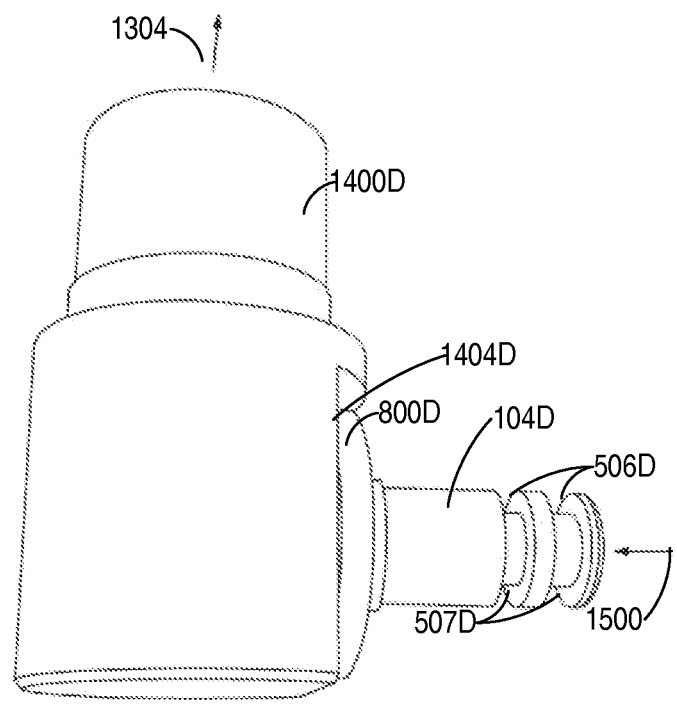
FIG. 15 is a side view of the elbow component with the nozzle outlet inserted.

Referring to FIG. 15, depicted is a side view of elbow component 1400D with nozzle outlet 104D inserted into opening 1404D. Nozzle outlet 104D has nozzle cap 700D attached as in FIG. 12. Gas leaves nozzle outlet 104D and enters opening 1404D in nozzle outlet direction 1500. Nozzle outlet direction 1500 may be perpendicular or substantially perpendicular to elbow component direction 1304. Again, a substantially perpendicular direction is within 20 degrees of perpendicular, between 70 and 110 degrees.

Figure 16:
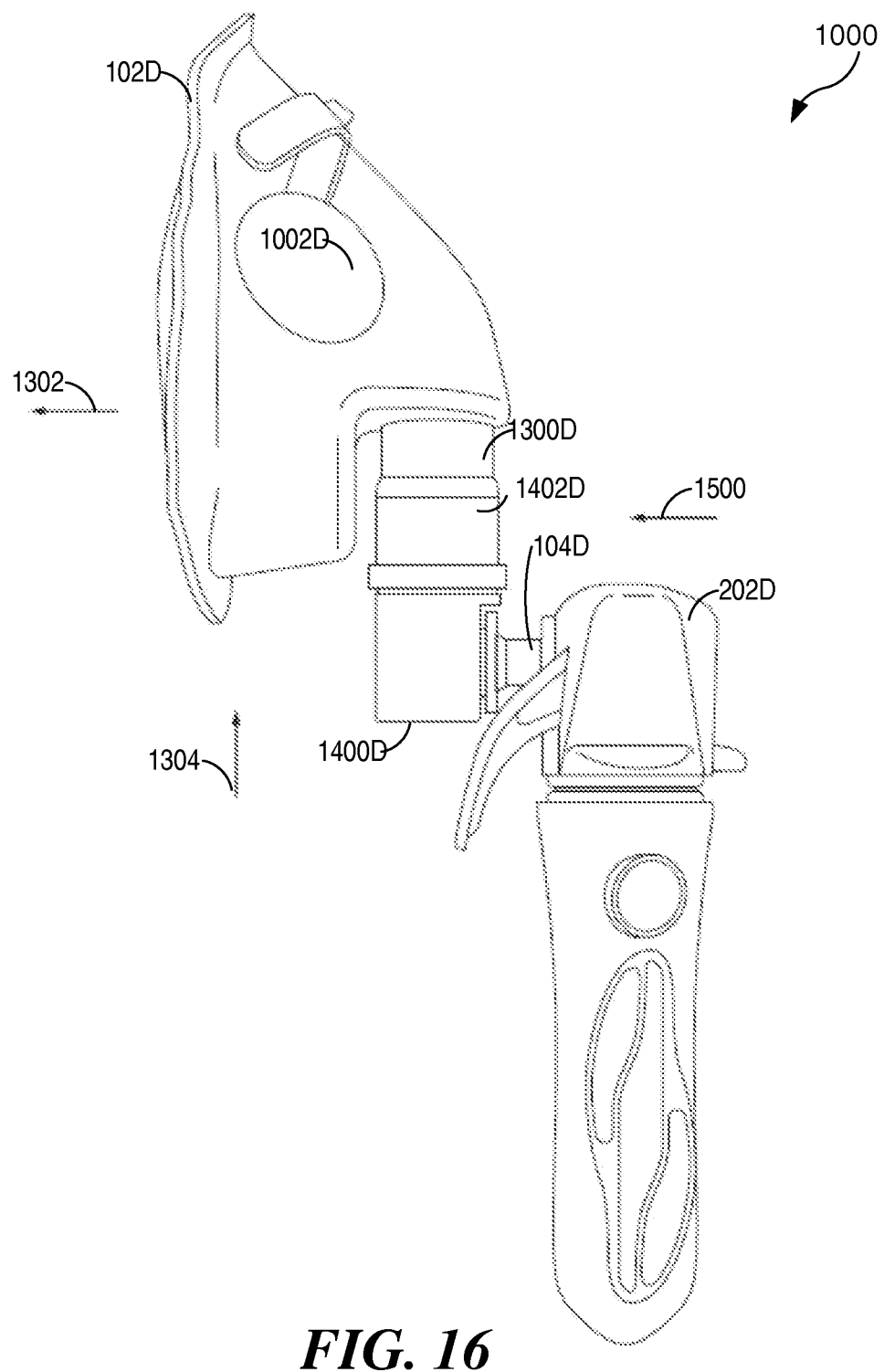
FIG. 16 is a side view of the fourth gas delivery device with the elbow component and mask affixed.

Referring to FIG. 16, depicted is a side view of gas delivery device 1000 with elbow component 1400D and mask 102D affixed. Elbow component 1400D forces the gas from nozzle outlet direction 1500 in elbow component direction 1304, out gas exit tube 1402D and into gas entry tube 1300D of mask 102D. The gas is inhaled and leaves mask 102D in mask opening direction 1302. If an ambient air hole 402D is open, the patient's inhalation may mix the gas with ambient air.

The roll pin in the device head permits nozzle outlet 104D to roll, and consequently elbow component 1400D and mask 102D to rotate, about the length of nozzle outlet 104D. Mask gas entry tube 1300D, and consequently the rest of mask 102D, may rotate about the length of gas exit tube 1402D.

Figure 17:
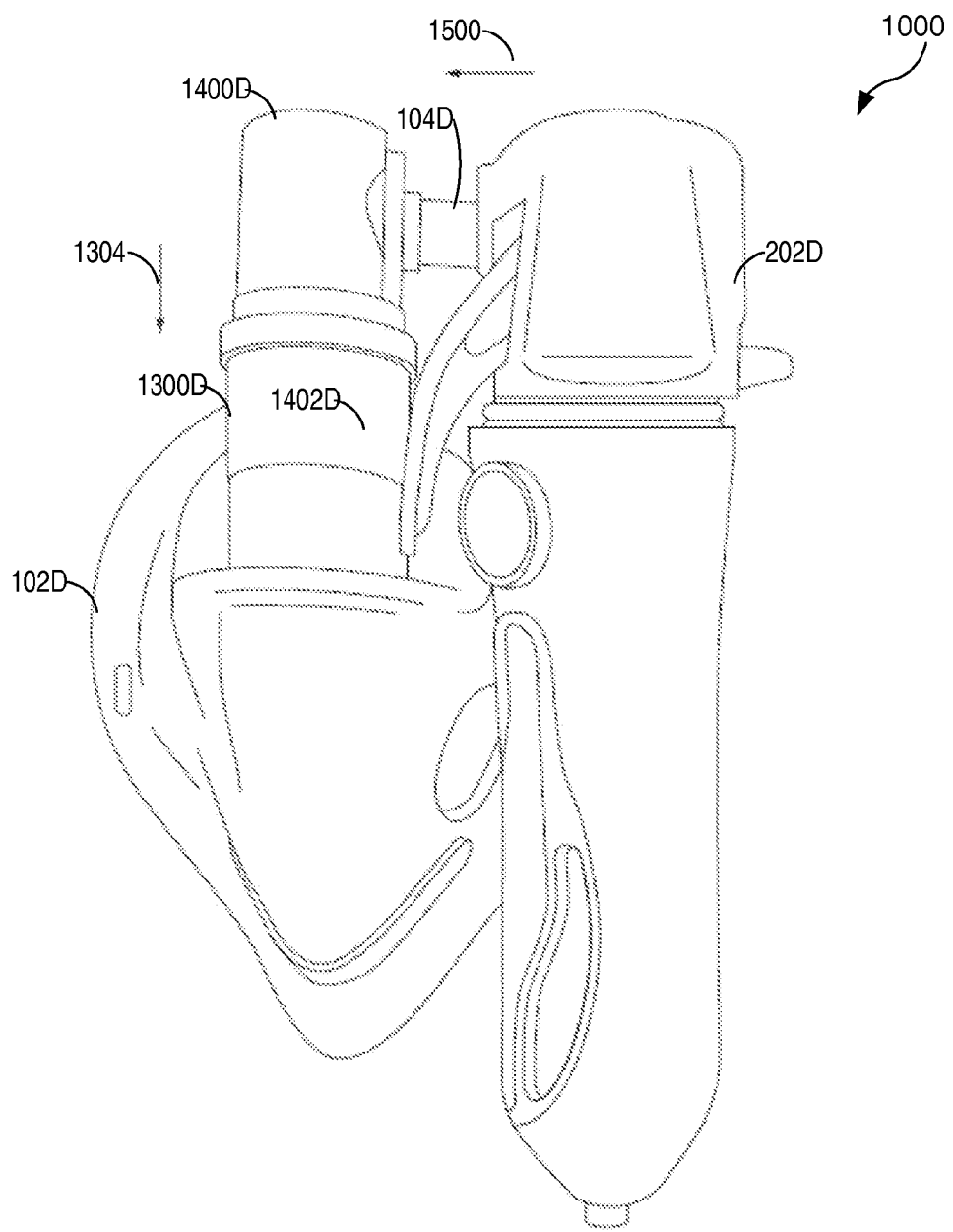
FIG. 17 is a side view of the fourth gas delivery device with the elbow component and mask affixed, in an alternate arrangement.

In the arrangement of FIG. 16, mask opening direction 1302 is nearly the same direction as nozzle outlet direction 1500, but this is not necessarily the case. Referring to FIG. 17, depicted is a side view of device 1000 in an alternate arrangement. Mask 102D has been rotated about the length of mask gas entry tube 1300D so that the mask opening direction is into the page. Further, nozzle outlet 104D has been rotated about its length so that mask 102D is upside-down, as permitted by the roll pin in head 202D.

Figure 18:
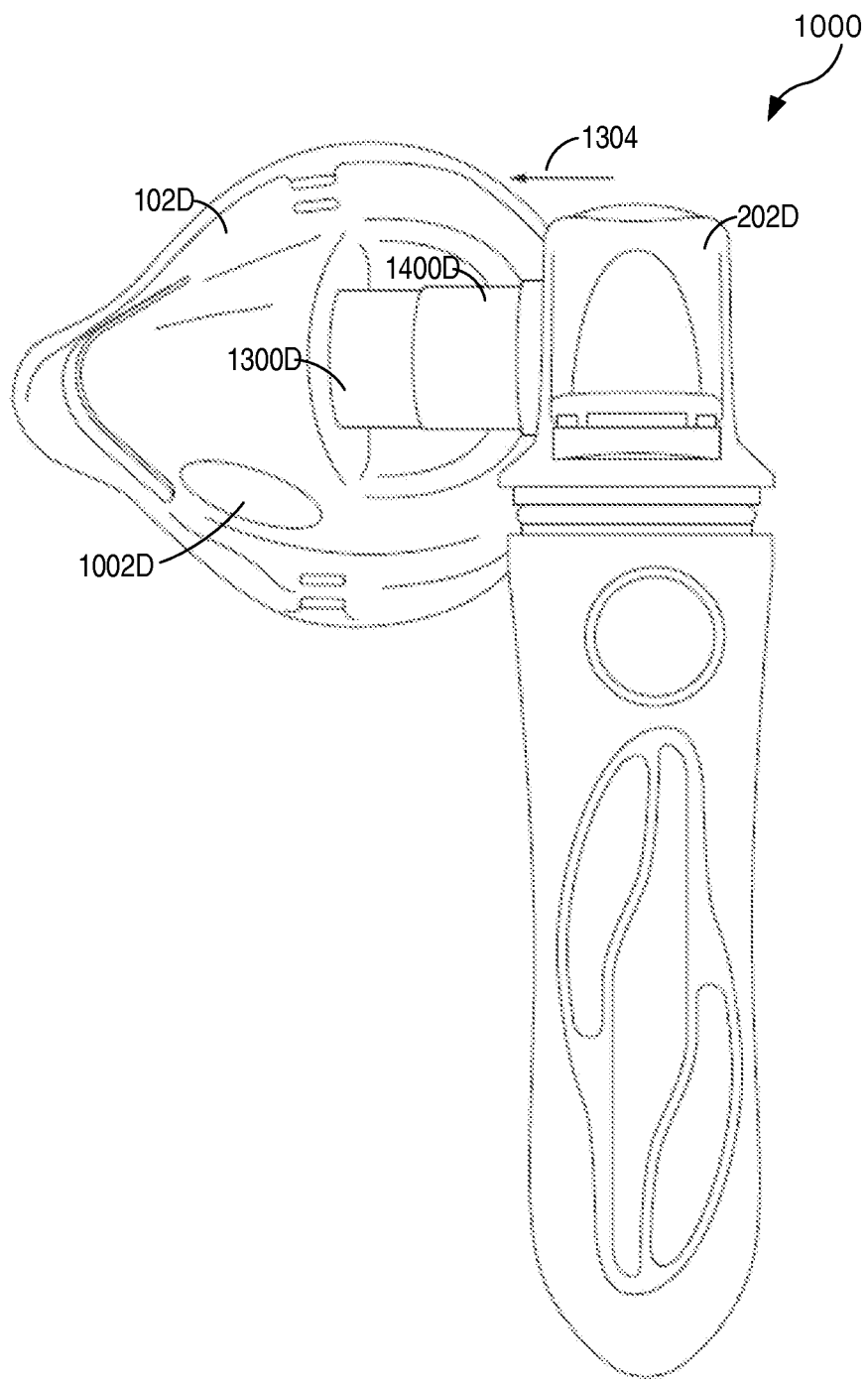
FIG. 18 is a side view of the fourth gas delivery device with the elbow component and mask affixed, in a second alternate arrangement.

Mask 102D has been rotated about the length of mask gas entry tube 1300D so that the mask opening direction is into the page. Nozzle outlet 104D has been rotated about its length Referring to FIG. 18, depicted is a side view of device 1000 in a second alternate arrangement. In the arrangement of FIG. 18, nozzle outlet direction 1500 and the mask opening direction are both now into the page. A patient lying on the patient's back would turn the patient's head to the side to breathe from mask 102D. Device 1000 would remain upright.

Figure 19:
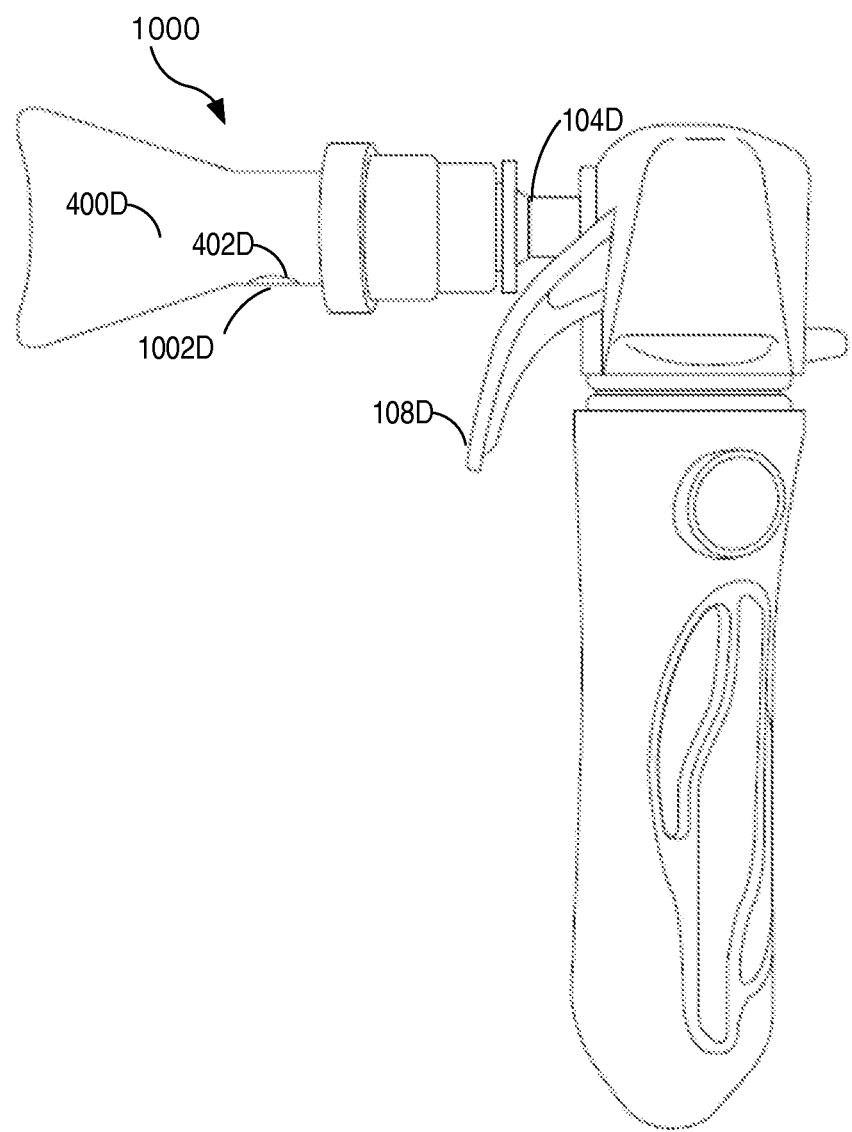
FIG. 19 is a side view of a fourth gas delivery device with a mouthpiece affixed, in a second alternate arrangement.

Referring to FIG. 19, depicted is a side view of device 1000 with a mouthpiece affixed as in FIG. 10, but in an alternate arrangement. Nozzle outlet 104D and the affixed mouthpiece 400D have been rotated approximately 90 degrees from their positions in FIG. 10. Again, this rotation is permitted by the roll pin in the device head. The roll pin holds nozzle outlet 104D in the device head but permits nozzle outlet 104D to rotate about the length of nozzle outlet 104D.

Figure 20:
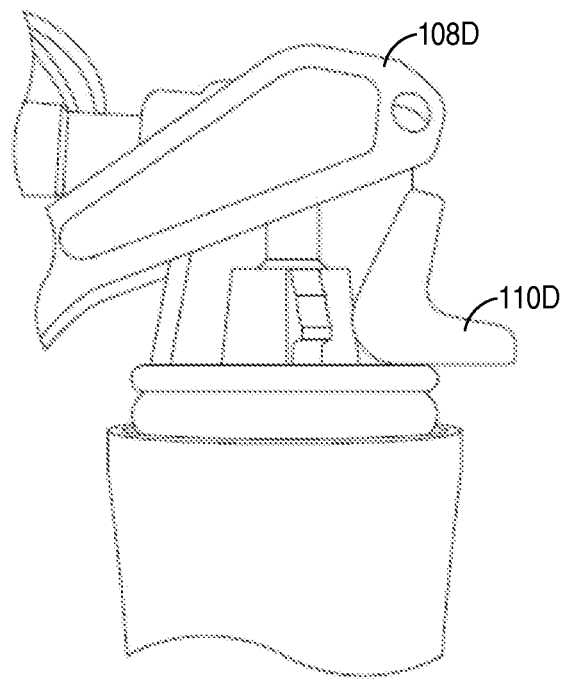
FIG. 20 is a side view of the locking mechanism of the fourth gas delivery device, with the locking mechanism in an unlocked position.
Figure 21:
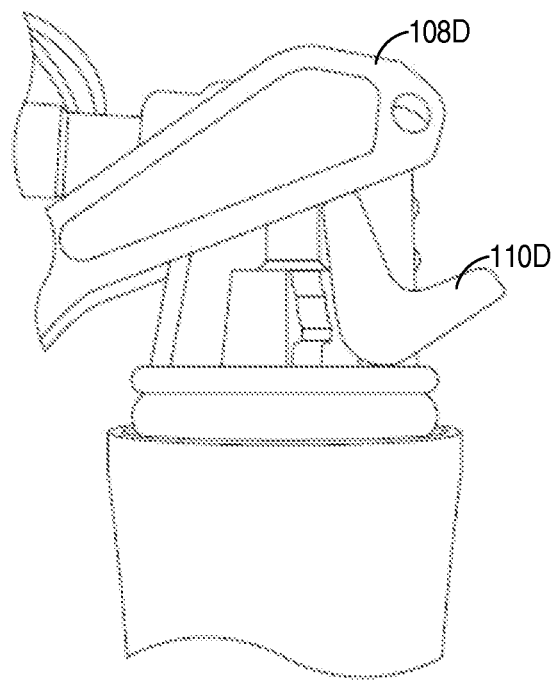
FIG. 21 is a side view of the locking mechanism of the fourth gas delivery device, with the locking mechanism in a locked position.

Referring to FIGS. 20 and 21, depicted are side views of the locking mechanism 110D of the fourth gas delivery device. The cover cap of the gas delivery device has been removed, showing all of the locking mechanism 110D. In FIG. 20, the locking mechanism 110D is in an unlocked position, while in FIG. 21 the locking mechanism 110D is in a locked position.

Locking mechanism 110D, like the locking mechanisms in the other gas delivery devices, places an obstruction, such as, but not limited to, a spacing member in a position under compression trigger 108D so as to make compression trigger 108D unable to release the gas. Locking mechanism 110D holding compression trigger 108D firmly up causes locking mechanism 110D to lock in place.

In practice, the preceding devices are designed to accommodate various sizes of individual use compressed gas cylinders, each cylinder having one or a combination of therapeutic gases therein. When a person or a mammal needs a quick dose of a mild, short acting therapeutic gas, such as for calming purposes, the person may unlock the locking mechanism, place the delivery component against their nose and/or mouth, and compress or depress the trigger in order to breathe in a continuous flow of the gas for a brief period. The devices may be disposable or replaceable. The devices may alternately be reusable.

Because the cylinders are relatively small, for example, holding 8, 12, or 16 grams there is very little likelihood of overdose or injury, even if the person is self-medicating. In most embodiments, the devices will be administered by licensed professionals to the person or mammal. In embodiments where it is used in other settings, such as professional settings, a larger capacity of gas may be appropriate, for example 24 grams.

The disclosed device and method represents the first means whereby a person or mammal can receive, on-demand and from a portable and handheld apparatus, an immediate acting, short lived, mild to moderate therapeutic agent to resolve undesirable feelings such as pain, anxiety, sleeplessness, stress, or other conditions. The handheld apparatus may be miniature or pocket-sized.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

It is to be understood that the embodiments disclosed herein are shown for illustrative purposes and are not intended to be construed as limitations of the disclosed method and system. Those skilled in the art will recognize or be able to ascertain in the course of routine experimentation, that variations and equivalents of the embodiments may be undertaken without departing from the scope of the invention.

Certain terms are used throughout the description to refer to particular method components. As one skilled in the art will appreciate, design and manufacturing companies may refer to a component by different names. This document does not intend to distinguish between components that differ in name but not function.

The terms "including" and "comprising" are used in an open-ended fashion, and thus should be interpreted to mean "including, but not limited to . . . . " Also, the term "couple" or "couples" is intended to mean either an indirect or direct connection. Thus, if a first device couples to a second device, that connection may be through a direct connection or through an indirect connection via other intermediate devices and connections. Moreover, the term "method" means "one or more components" combined together. Thus, a method can comprise an "entire method" or "sub methods" within the method.

The use of the word "a" or "an" when used in conjunction with the word "comprising" may mean "one", or may also mean "one or more." The use of the term "or" in the claims is used to mean "and/or" unless explicitly indicated to refer to alternatives only or the alternatives are mutually exclusive, although the disclosures supports a definition that refers to only alternatives and "and/or."

The methods and systems disclosed and claimed herein can be made and executed without undue experimentation based on the level of disclosure presented. While the methods and systems have been described in terms of their preferred embodiments, it will be apparent to those skilled in the art that they are not limited to the exact steps described and may vary from such description without departing from the scope and spirit of the invention. The substitutes and modifications employed by one skilled in the art are deemed to fall within the scope of the invention.

I claim:

1. A nozzle apparatus for dispensing an adjustable combination of gas, the nozzle apparatus comprising:
   a roll pin;
   a nozzle outlet comprising:
      a groove for receiving the roll pin, wherein the groove is disposed along at least a portion of the perimeter of the nozzle outlet and configured to allow rotation of the nozzle outlet about its lengthwise axis and relative to the roll pin; and
      an inner lumen comprising a cylindrical shaft having a diameter between $5/1000$ths and $20/1000$ths of an inch;
   a triggering device configured to be movable from an unactuated first position to an actuated second position, wherein gas is permitted to flow through the inner lumen when the triggering device is moved to the actuated second position;

a spring member operably connected to the triggering device and configured to urge the triggering device towards the unactuated first position, wherein a user of the nozzle apparatus must exert a force to oppose the urging force of the spring member to move the triggering device from the unactuated first position to the actuated second position; and a delivery component configured to receive gas from the nozzle outlet, the delivery component comprising:
    a first circular ambient air hole having a diameter;
    a second circular ambient air hole having the same diameter as the first ambient air hole; and
    one or more removable plugging devices covering the ambient air holes.

2. The nozzle apparatus of claim 1, wherein the nozzle outlet further comprises a nozzle cap covering an end of the nozzle outlet, the nozzle cap comprising a debris filter having one or more holes.

3. The nozzle apparatus of claim 2, wherein the nozzle cap is removably affixed to the end of the nozzle outlet, and further comprising a particle filter within the nozzle outlet.

4. The nozzle apparatus of claim 1, wherein:
the delivery component comprises a mouthpiece comprising an inhalation tube; and the diameter of the first ambient air hole and the second ambient air hole is between 0.18 and 0.38 inches.

5. The nozzle apparatus of claim 1, wherein:
the delivery component comprises a mask; and
the diameter of the first ambient air hole and the second ambient air hole is between 0.5 and 0.9 inches.

6. The nozzle apparatus of claim 5, further comprising:
an elbow component, comprising:
an inlet configured to removably couple to the nozzle outlet; and
a gas exit tube extending away from the inlet in a direction substantially perpendicular to the nozzle outlet direction; and
wherein the mask further comprises:
    a mask opening in a mask opening direction, the mask opening direction substantially perpendicular to the gas exit tube direction; and
    a gas entry tube receiving the gas exit tube.

7. The nozzle apparatus of claim 1, wherein while the triggering device is in the actuated second position, a continuous flow of gas is provided to the delivery component.

8. The nozzle apparatus of claim 7, further comprising a locking mechanism configured to move between a locked first position and an unlocked second position, wherein while in the locked first position, the locking mechanism is configured to prevent movement of the trigger from the unactuated first position to the actuated second position, and wherein while in the unlocked second position, the locking mechanism is configured to allow movement of the trigger from the unactuated first position to the actuated second position.

9. The nozzle apparatus of claim 1, further comprising:
a cylinder holding a supply of gas;
a housing configured to form an enclosure around the cylinder; and
a head portion of the nozzle apparatus configured to allow for the cylinder and housing to removably couple to the nozzle apparatus.

10. The nozzle apparatus of claim 9, wherein the housing further comprises a transparent viewing window.

11. The nozzle apparatus of claim 1, wherein the nozzle outlet further comprises a retaining lip disposed along at least a portion of the nozzle outlet perimeter, wherein the retaining lip is configured to maintain the delivery component at a distance from the triggering mechanism sufficient to prevent the triggering mechanism from interfering with the delivery component during rotation of the delivery component about the lengthwise axis of the nozzle outlet and while the triggering mechanism is in the unactuated first position.

12. A method for dispensing an adjustable concentration of gas, the method comprising steps of:
receiving a delivery component, the delivery component comprising one or more ambient air holes, each having substantially the same diameter, wherein the one or more ambient air holes are covered, as desired, by one or more removable plugging devices to set the concentration of gas delivered at desired concentration;
receiving a nozzle outlet, the nozzle outlet comprising:
    a groove for receiving a roll pin, wherein the groove is disposed along at least a portion of the perimeter of the nozzle outlet and configured to allow rotation of the nozzle outlet about its lengthwise axis and relative to the roll pin; and
    an inner lumen comprising a cylindrical shaft having a diameter between $5/1000$ths and $20/1000$ths of an inch;
affixing the delivery component to the nozzle outlet, wherein the delivery component is configured to rotate with the nozzle outlet about the lengthwise axis of the nozzle outlet and relative to the roll pin;
exerting a force to move a triggering mechanism from an unactuated first position to an actuated second position to initiate a continuous flow of gas to the delivery component while the triggering mechanism is in the actuated second position, wherein the trigger mechanism is configured to remain in the unactuated first position in the absence of application of said force.

13. The method of claim 12, wherein the nozzle outlet further comprises a retaining lip, and wherein affixing the delivery component to the nozzle outlet comprises sliding the delivery component over the nozzle outlet until the delivery component is flush against the retaining lip.

14. The method of claim 13, further comprising rotating the mask about the length of the gas exit tube, wherein the retaining lip is disposed along at least a portion of the nozzle outlet perimeter, and wherein the retaining lip is configured to maintain the mask at a distance from the triggering mechanism sufficient to prevent the triggering mechanism from interfering with the mask during rotation of the mask about the lengthwise axis of the nozzle outlet and while the triggering mechanism is in the unactuated first position.

15. The method of claim 12, further comprising covering an end of the nozzle outlet with a nozzle cap, the nozzle cap comprising a debris filter having one or more holes.

16. The method of claim 15, further comprising placing a particle filter inside the nozzle outlet.

17. The method of claim 12, wherein:
the delivery component comprises a mouthpiece comprising an inhalation tube; and
the diameter of the first ambient air hole and the second ambient air hole is between 0.18 and 0.38 inches.

18. The method of claim 12, wherein:
the delivery component comprises a mask; and
the diameter of the first ambient air hole and the second ambient air hole is between 0.5 and 0.9 inches.

19. The method of claim 18, wherein affixing the mask to the nozzle outlet comprises:
affixing the nozzle outlet to an elbow component, the elbow component receiving the nozzle outlet in a nozzle outlet direction, the elbow component comprising a gas exit tube substantially perpendicular to the nozzle outlet direction; and affixing a gas entry tube of the mask to the gas exit tube;
wherein the mask further comprises a mask opening in a mask opening direction, the mask opening direction substantially perpendicular to the elbow component direction.

20. The method of claim 19, further comprising rotating the mask about the length of the gas exit tube.

21. A portable, handheld gas delivery apparatus for delivery of a configurable mixture of ambient air and a therapeutic gas, comprising:
- a cylinder providing a supply of a therapeutic gas;
- a nozzle, further comprising:
  - a trigger configured to be movable from an unactuated first position to an actuated second position, wherein the therapeutic gas is permitted to flow through the nozzle when the trigger is moved to the actuated second position;
  - a locking mechanism configured to move between a locked first position and an unlocked second position, wherein while in the locked first position, the locking mechanism prevents movement of the trigger to the actuated second position, and wherein while in the unlocked second position, the locking mechanism is configured to allow movement of the trigger from the unactuated first position to the actuated second position;
  - a lumen providing an opening of a fixed area through which the therapeutic gas flows;
  - a roll pin; and
  - an outlet having a groove along substantially the entire perimeter of the outlet for receiving the roll pin, wherein the groove and roll pin allow for the outlet to rotate about the lengthwise axis of the outlet and relative to the roll pin;
- a delivery component further comprising:
  - one or more holes for allowing ambient air to enter the delivery component and mix with the therapeutic gas; and
  - one or more plugging devices configured for removable coupling to the one or more holes;
- wherein the delivery component rotates with the outlet about the lengthwise axis of the outlet and relative to the roll pin;
- wherein the delivery component is further configured to removably attach to the nozzle, allowing for interchangeable use of a plurality of delivery components with the nozzle; and
- wherein the concentration of therapeutic gas delivered is configurable through variation of only the open area provided by the one or more holes.

22. The gas delivery apparatus of claim 21, wherein the mixture of ambient air and therapeutic gas is configurable through the use of interchangeable delivery components, each having a one or more holes configuration of a size and quantity, thereby allowing the amount of ambient air entering the delivery component and mixing with the gas to be varied while the amount of gas provided to the delivery component remains fixed.

23. The gas delivery apparatus of claim 21, wherein the open area through which ambient air may enter the delivery component is configurable through use of the one or more plugging devices to block ambient air from entering the delivery component through a desired quantity of the one or more holes of the delivery component.

24. The gas delivery apparatus device of claim 21, further comprising a cap having a debris filter and one or more holes, configured to be removably coupled to the outlet.

25. The gas delivery apparatus of claim 21, further comprising a particle filter contained within the outlet.

26. The gas delivery apparatus of claim 21, wherein while the trigger is in the actuated second position, a continuous flow of therapeutic gas is provided to the delivery component.

27. The gas delivery apparatus of claim 21, further comprising a housing configured to couple to the nozzle and form an enclosure around the cylinder.

28. The gas delivery apparatus of claim 21, wherein the outlet further comprises a retaining lip along at least a portion of the outlet perimeter, configured to maintain the delivery component at a distance from the trigger sufficient to prevent the delivery component from contacting the trigger when the trigger is in the unactuated first position as the outlet and delivery component rotate.

29. The gas delivery apparatus of claim 28, further comprising an elbow component, comprising:
- an inlet configured to removeably couple to the outlet of the nozzle; and
- an exit tube extending away from the inlet in a direction substantially perpendicular to the longitudinal direction of the outlet of the nozzle;
- wherein the elbow component is configured to rotate with the outlet.

30. the apparatus of claim 21, wherein the one or more plugging devices is a removable sticker.

* * * * *